(12) United States Patent
Leabman

(10) Patent No.: US 11,298,037 B2
(45) Date of Patent: Apr. 12, 2022

(54) SYSTEMS FOR MULTI-BAND RADAR BASED SENSING

(71) Applicant: MOVANO INC., San Ramon, CA (US)

(72) Inventor: Michael A. Leabman, San Ramon, CA (US)

(73) Assignee: Movano Inc., Pleasanton, CA (US)

( * ) Notice: Subject to any disclaimer, the term of this patent is extended or adjusted under 35 U.S.C. 154(b) by 341 days.

(21) Appl. No.: 16/719,134

(22) Filed: Dec. 18, 2019

(65) Prior Publication Data

US 2020/0191933 A1    Jun. 18, 2020

Related U.S. Application Data

(60) Provisional application No. 62/781,523, filed on Dec. 18, 2018.

(51) Int. Cl.
*A61B 5/0245* (2006.01)
*H04B 7/08* (2006.01)
(Continued)

(52) U.S. Cl.
CPC ............ *A61B 5/0245* (2013.01); *A61B 5/021* (2013.01); *A61B 5/0205* (2013.01);
(Continued)

(58) Field of Classification Search
CPC ..... A61B 5/0245; A61B 5/0205; A61B 5/021; A61B 5/02141; A61B 5/02444;
(Continued)

(56) References Cited

U.S. PATENT DOCUMENTS 6,128,276 A    10/2000    Agee
6,512,737 B1    1/2003    Agee
(Continued)

FOREIGN PATENT DOCUMENTS

WO    2007/014333 A2    2/2007
WO    2010131029 A1    11/2010
(Continued)

OTHER PUBLICATIONS

American Diabetes Association, "Economic Costs of Diabetes in the U.S. in 2017", https://doi.org/10.2337/dci18-0007, Mar. 22, 2018, 12 pgs.

(Continued)

*Primary Examiner* — Vladimir Magloire
*Assistant Examiner* — Yonghong Li
(74) *Attorney, Agent, or Firm* — Loza & Loza, LLP

(57) ABSTRACT

Devices, systems, and methods for multi-band radar sensing are disclosed. In an embodiment, an integrated circuit device includes transmit components and receive components, a low-band transmit interface connected to output a first signal at a low-band frequency, a high-band transmit interface connected to output a second signal at a high-band frequency, a low-band receive interface connected to receive a third signal at the low-band frequency, a high-band receive interface connected to receive a fourth signal at the high-band frequency, and mixers connected to upconvert the first signal at the low-band frequency to the second signal at the high-band frequency for transmission from the high-band transmit interface and to downconvert the fourth signal at the high-band frequency received at the high-band receive interface to a fifth signal at the low-band frequency, wherein the upconversion and the downconversion are implemented using a conversion signal at a conversion frequency.

32 Claims, 15 Drawing Sheets

(51) Int. Cl.

| | |
|---|---|
| *H04B 7/06* | (2006.01) |
| *A61B 5/00* | (2006.01) |
| *A61B 5/145* | (2006.01) |
| *A61B 5/021* | (2006.01) |
| *A61B 5/05* | (2021.01) |
| *G01S 7/03* | (2006.01) |
| *G01S 13/02* | (2006.01) |
| *G01S 13/26* | (2006.01) |
| *A61B 5/024* | (2006.01) |
| *G01S 13/88* | (2006.01) |
| *A61B 5/0205* | (2006.01) |
| *G01S 13/76* | (2006.01) |
| *H03D 7/16* | (2006.01) |
| *H04B 1/04* | (2006.01) |
| *G01S 7/02* | (2006.01) |

(52) U.S. Cl.
CPC ...... *A61B 5/02141* (2013.01); *A61B 5/02444* (2013.01); *A61B 5/05* (2013.01); *A61B 5/14532* (2013.01); *A61B 5/489* (2013.01); *A61B 5/681* (2013.01); *A61B 5/6898* (2013.01); *A61B 5/725* (2013.01); *A61B 5/7207* (2013.01); *A61B 5/7257* (2013.01); *A61B 5/742* (2013.01); *G01S 7/03* (2013.01); *G01S 7/032* (2013.01); *G01S 13/0209* (2013.01); *G01S 13/26* (2013.01); *G01S 13/76* (2013.01); *G01S 13/88* (2013.01); *H03D 7/168* (2013.01); *H04B 1/04* (2013.01); *H04B 7/06* (2013.01); *H04B 7/0617* (2013.01); *H04B 7/08* (2013.01); *G01S 7/028* (2021.05); *G01S 2013/0245* (2013.01); *H04B 2001/0491* (2013.01)

(58) Field of Classification Search
CPC ....... A61B 5/05; A61B 5/14532; A61B 5/489; A61B 5/681; A61B 5/6898; A61B 5/7207; A61B 5/725; A61B 5/7257; A61B 5/742; A61B 5/024; A61B 5/0507; G01S 7/03; G01S 13/76; G01S 13/88; G01S 7/028; G01S 7/032; G01S 13/0209; G01S 13/26; G01S 2013/0245; H03D 7/168; H04B 1/04; H04B 7/06; H04B 7/0617; H04B 7/08; H04B 2001/0491; H04B 1/385; H04B 7/086; H04B 2001/3855; H04B 2001/3861
See application file for complete search history.

(56) References Cited

U.S. PATENT DOCUMENTS

| | | | |
|---|---|---|---|
| 6,664,920 | B1 | 12/2003 | Mott et al. |
| 7,936,301 | B2 | 5/2011 | Niedzwiecki |
| 9,408,564 | B2 | 8/2016 | Porch et al. |
| 9,575,560 | B2 | 2/2017 | Poupyrev et al. |
| 10,092,207 | B1 | 10/2018 | Windmiller |
| 10,398,370 | B2 | 9/2019 | Boshra et al. |
| 10,478,099 | B2 | 11/2019 | Lor et al. |
| 2003/0114188 | A1 | 6/2003 | Rousu |
| 2003/0171101 | A1* | 9/2003 | Suzuki .................. H04B 1/406 455/147 |
| 2003/0207668 | A1 | 11/2003 | Mcfarland et al. |
| 2004/0192223 | A1 | 9/2004 | Gardenfors et al. |
| 2004/0204036 | A1 | 10/2004 | Yang |
| 2008/0169961 | A1 | 7/2008 | Steinway et al. |
| 2008/0319285 | A1 | 12/2008 | Hancock |
| 2010/0324398 | A1 | 12/2010 | Tzyy-Ping |
| 2011/0221519 | A1 | 9/2011 | Katoh et al. |
| 2012/0150000 | A1 | 6/2012 | Al-Shamma'a et al. |
| 2013/0297223 | A1 | 11/2013 | Fischer |
| 2014/0134959 | A1* | 5/2014 | Tasic .................. H04B 1/18 455/73 |
| 2015/0263777 | A1 | 9/2015 | Fraden |
| 2016/0041617 | A1 | 2/2016 | Poupyrev |
| 2016/0051171 | A1 | 2/2016 | Pikov et al. |
| 2016/0072933 | A1 | 3/2016 | Cox, II |
| 2016/0097716 | A1 | 4/2016 | Gulati et al. |
| 2016/0231236 | A1 | 8/2016 | Gulati et al. |
| 2016/0252607 | A1 | 9/2016 | Saboo et al. |
| 2016/0320852 | A1 | 11/2016 | Poupyrev |
| 2017/0023673 | A1 | 1/2017 | Mansour et al. |
| 2017/0156646 | A1 | 6/2017 | Gulati et al. |
| 2017/0164878 | A1 | 6/2017 | Connor |
| 2017/0238835 | A1 | 8/2017 | Melamed |
| 2017/0285135 | A1* | 10/2017 | Valentine ................ G01S 7/285 |
| 2018/0046258 | A1 | 2/2018 | Poupyrev |
| 2018/0103906 | A1 | 4/2018 | Gandhi et al. |
| 2018/0120420 | A1 | 5/2018 | Mcmahon et al. |
| 2018/0196134 | A1 | 7/2018 | Safavi-Naeini et al. |
| 2018/0217252 | A1 | 8/2018 | Noujeim et al. |
| 2018/0303386 | A1 | 10/2018 | Hall et al. |
| 2018/0303417 | A1 | 10/2018 | Mensinger et al. |
| 2018/0306723 | A1 | 10/2018 | Ashrafi |
| 2018/0307314 | A1 | 10/2018 | Connor |
| 2018/0322351 | A1 | 11/2018 | Shaker |
| 2018/0348341 | A1 | 12/2018 | Phelan et al. |
| 2019/0008422 | A1 | 1/2019 | Leath et al. |
| 2019/0064342 | A1 | 2/2019 | Daisy et al. |
| 2019/0064344 | A1 | 2/2019 | Turner |
| 2019/0095602 | A1 | 3/2019 | Setlak et al. |
| 2019/0101870 | A1 | 4/2019 | Pandya et al. |
| 2019/0117068 | A1 | 4/2019 | Thomson et al. |
| 2019/0219368 | A1 | 7/2019 | Baheti et al. |
| 2019/0257933 | A1 | 8/2019 | Nath et al. |
| 2019/0290161 | A1 | 9/2019 | Chase |
| 2019/0298265 | A1 | 10/2019 | Keating et al. |
| 2020/0133398 | A1 | 4/2020 | Williams et al. |

FOREIGN PATENT DOCUMENTS

| | | |
|---|---|---|
| WO | 2017111623 A1 | 6/2017 |
| WO | 2018123204 A1 | 7/2018 |

OTHER PUBLICATIONS

Bruen, Danielle et al. "Glucose Sensing for Diabetes Monitoring: Recent Developments", Sensors 2017, 21 pgs.

Cano-Garcia, Helena et al. "Millimeter-Wave Sensing of Diabetes-Relevant Glucose Concentration Changes in Pigs", J Infrared Milli Terahz Waves (2018) 39: pp. 761-772.

Cespedes, Fabiola Araujo, "RF Sensing System for Continous Blood Blucose Monitoring", Nov. 2017, 121 pgs.

Cheggoju, Shiva Prasad, "Development of Non-Invasive Glucos Sensor", A Thesis Presented to The Graduate Faculty of the University of Akron, May 2016, 80 pgs.

Droitcour, Amy Diane, "Non-Contact Measurement of Heat and Respiration Rates with a Single-Chip Microwave Doppler Radar", A Dissertation Submitted to the Department of Electrical Engineering and the Committee on Graduate Studies of Stanford University, Jun. 2006, 470 pgs.

Gia, Tuan Nguyen, "IoT-based continuous glucose monitoring system: A feasibility study", 8th International Conference on Ambient Systems, Networks and Technologies (ANT-2017), pp. 327-334.

Girão, P. Silva et al. "Microwave Doppler radar in unobtrusive health monitoring", Journal of Physics: Conference Series, file:///C:/Users/Mark%20Wilson/Downloads/Microwave_Doppler_radar_in_unobtrusive_health_moni.pdf, retrieved Oct. 22, 2018, 11 pgs.

Gonzales, Wilbert Villena, "The Progress of Glucose Monitoring—A Review of Invasive to Minimally and Non-Invasive Tehniques, Devices and Sensors", Sensors 2019, 45 pgs.

IHS, "Wearables and Glucose Monitoring" The New Frontier in Diabetes Management, file:///C:/Users/Mark%20Wilson/Downloads/wearables-and-glucose-monitoring%20(1).pdf, retrieved Jun. 19, 2020, 6 pgs.

(56) References Cited

OTHER PUBLICATIONS

Jain, Vipul et al. "A Single-Chip Dual-Band 22-29-GHz/77-81-GHz BiCMOS Transceiver for Automotive Radars", IEEE 2009, 17 pgs.

Klaric-Felic, Gordana et al. "Single-Chip Millimeter-Wave Radar", Article in Microwave Journal—Jan. 2015, 10 pgs.

Lien, Jaime, "Soli: Ubiquitous Gesture Sensing with Millimeter Wave Radar", ACM Trans, Graph, vol. 35, No. 4, Article 142, Jul. 2016, 19 pgs.

Mazlouman, Shahrzad Jalaliet al. Contact-less Monitoring of the Major Blood Vessels Supplying Head and Brain (Carotid Arteries), NSTI-Nanotech 2009, 4 pgs.

Nasr, Ismail et al. "A Highly Integrated 60 GHz 6-Channel transceiver with Antenna in Package for Smart Sensing and Short-Range Communications" IEEE Journal of Solid-State Circuits, vol. 51, No. 9, Sep. 2016, pp. 2066-2076.

Nahar, Sabikun, "Design and Implementation of a Stepped Frequency Continous Wave Radar System for Biomedical Applications", Masters Theses, University of Tennessee, Knoxville, 85 pgs.

Omer, Ala Eldin et al. "Blood Glucose Level Monitoring Using and FMCW Millimeter-Wave Radar Sensor", Remote Sensing, 2020, 25 pgs.

Omer, Ala Eldin et al. "Glucose Levels Detection Using mm-Wave Radar", SensorsLetters, vol. 2, No. 3, Sep. 2018, 5 pgs.

Ram, Suresh et al. "Compact Radar Form Factors Accelerate commercial Adoption", Microwaves & RF, Jul. 2016, 2 pgs.

Saha, Shimul et al. "A Glucose sensing System Based on Transmission Measurements at Millimetre Waves using Micro strip Patch Antennas", Scientific Reports 7:6855, 11 pgs.

Shaker, George et al. "Non-Invasive Monitoring of Glucose Level Changes Utilizing a mm-Wave Radar System", International Journal of Mobile Human Computer Interaction, vol. 10, issue 3, Jul.-Sep. 2018, 20 pgs.

Siegel, Peter H. et al. "Millimeter-Wave Non-Invasive Monitoring of Glucose in Anesthetized Rats", International Conference on Infrared, Millimeter, and Terhaertz Waves, Tucson, AZ, Sep. 14-19, 2014, 2 pgs.

Smith, John L., "The Pursuit of Noninvasive Glucose: "Hunting the Deceitful Turkey"", Sixth Edition Revised and Expanded, 2018, 225 pgs.

Torp, Hans "Signal processing in Ultrasound Doppler and Color Flow Imaging", http://folk.ntnu.no/htorp/Undervisning/FlowMeas02/papers/EstBloodVel.pdf, retrieved Jun. 19, 2020, 22 pgs.

Yi, Xiang et al. "A 24/77 GHz Dual-Band Receiver for Automotive Radar Applications", vol. 7, 2019, pp. 48053-48059.

Yilmaz, Tuba et al. "Radio-Frequency and Microwave Techniques for Non-Invasive Measurement of Blood Glucose Levels", Diagnosis 2019, 34 pgs.

Nahar, Sabikun, "Design and Implementation of a Stepped Frequency Continous Wave Radar System for Biomedical Applications", Masters Theses, University of Tennessee, Knoxville, Aug. 2018, 85 pgs.

Saha, Shimul et al. "A Glucose sensing System Based on Transmission Measurements at Millimetre Waves using Micro strip Patch Antennas", Scientific Reports 7:6855, Jul. 31, 2017, 11 pgs.

Extended European Search Report for EP19900070.4 dated Nov. 15, 2021, 2 pgs.

Written Opinion for cooresponding Extended European Search Report, EP19900070.4, dated Nov. 15, 2021, 6 pages.

International Search Report and Written Opinion, PCT/US19/67273, dated Apr. 9, 2020.

Non-Final Office Action; U.S. Appl. No. 16/719,394; 21 pages (dated Jul. 30, 2020).

* cited by examiner

SYSTEMS FOR MULTI-BAND RADAR BASED SENSING

BACKGROUND

Radar detection involves transmitting electromagnetic energy and receiving reflected portions of the transmitted electromagnetic energy. Techniques for transmitting electromagnetic energy in radar systems include impulse, chirp, and stepped frequency techniques. Stepped frequency radar has traditionally been implemented by repeatedly scanning over the same frequency range using the same step size. For example, a frequency burst of stepped frequency pulses over the same frequency range with the same step size and the same number of steps is continuously repeated to implement stepped frequency radar. Although traditional stepped frequency radar works well, there is a need to expand the capabilities of stepped frequency radar.

SUMMARY

Devices, systems, and methods for multi-band radar sensing are disclosed. In an embodiment, an integrated circuit device includes transmit components and receive components, at least one low-band transmit interface connected to a first transmit component to output a first signal at a low-band frequency, at least one high-band transmit interface connected to a second transmit component to output a second signal at a high-band frequency, at least one low-band receive interface connected to a first receive component to receive a third signal at the low-band frequency, at least one high-band receive interface connected to a second receive component to receive a fourth signal at the high-band frequency, and mixers connected to upconvert the first signal at the low-band frequency to the second signal at the high-band frequency for transmission from the high-band transmit interface and to downconvert the fourth signal at the high-band frequency received at the high-band receive interface to a fifth signal at the low-band frequency, wherein the upconversion and the downconversion are implemented using a conversion signal at a conversion frequency. In an embodiment, the low-band frequency is in the range of 2-6 GHz, the high-band frequency is in the range of 122-126 GHz, and the conversion frequency is 120 GHz. In another embodiment, the low-band frequency is in the range of 2-6 GHz, the high-band frequency is in the range of 22-26 GHz, and the conversion frequency is 20 GHz.

In an embodiment, the integrated circuit device further includes a second receive mixer connected to upconvert the first signal at the low-band frequency with an intermediate frequency to output a sixth signal at the low-band frequency plus the intermediate frequency. In a further embodiment, the integrated circuit device also includes a third receive mixer connected to downconvert the third signal at the low-band frequency and the fifth signal at the high-band frequency with the sixth signal at the low-band frequency plus the intermediate frequency to produce a seventh signal at the intermediate frequency.

Another embodiment of an integrated circuit device is disclosed. The integrated circuit device includes transmit components and receive components, at least one low-band transmit interface connected to a first transmit component to output a first signal at a low-band frequency, at least one high-band transmit interface connected to a second transmit component to output a second signal at a high-band frequency, at least one low-band receive interface connected to a first receive component to receive a third signal at the low-band frequency, at least one high-band receive interface connected to a second receive component to receive a fourth signal at the high-band frequency, and means for upconverting the first signal at the low-band frequency to the second signal at the high-band frequency for transmission from the high-band transmit interface and downconverting the fourth signal at the high-band frequency received at the high-band receive interface to a fifth signal at the low-band frequency, wherein the upconversion and the downconversion are implemented using a conversion signal at a conversion frequency.

Another embodiment of an integrated circuit device is disclosed. The integrated circuit device includes transmit components and receive components, at least one low-band transmit interface connected to a first transmit component to output a first signal at a low-band frequency, at least one high-band transmit interface connected to a second transmit component to output a second signal at a high-band frequency, at least one low-band receive interface connected to a first receive component to receive a third signal at the low-band frequency, at least one high-band receive interface connected to a second receive component to receive a fourth signal at the high-band frequency, a transmit mixer connected to upconvert the first signal at the low-band frequency to the second signal at the high-band frequency for transmission from the high-band transmit interface, and a receive mixer connected to downconvert the fourth signal at the high-band frequency received at the high-band receive interface to a fifth signal at the low-band frequency, wherein the transmit mixer and the receive mixer are connected to receive a conversion signal at a conversion frequency.

Another embodiment of an integrated circuit device is disclosed. The integrated circuit device includes transmit components and receive components, at least one low-band transmit interface connected to a first transmit component to output a first signal at a low-band frequency, at least one medium-band transmit interface connected to a second transmit component to output a second signal at a medium-band frequency, at least one high-band transmit interface connected to a third transmit component to output a third signal at a high-band frequency, at least one low-band receive interface connected to a first receive component to receive a fourth signal at the low-band frequency, at least one medium-band receive interface connected to a second receive component to receive a fifth signal at the medium-band frequency, at least one high-band receive interface connected to a third receive component to receive a sixth signal at the high-band frequency, and mixers connected to upconvert the first signal at the low-band frequency to the second signal at the medium-band frequency for transmission from the medium-band transmit interface, to upconvert the first signal at the low-band frequency to the third signal at the high-band frequency for transmission from the high-band transmit interface, and to downconvert the fifth signal at the medium-band frequency received at the medium-band receive interface to a seventh signal at the low-band frequency and to downconvert the sixth signal at the high-band frequency received at the high-band receive interface to an eighth signal at the low-band frequency, wherein the upconversion and the downconversion corresponding to the medium-band frequency are implemented using a conversion signal at a first conversion frequency and wherein the upconversion and the downconversion corresponding to the high-band frequency are implemented using a conversion signal at a second conversion frequency.

An embodiment of an RF system is disclosed. The RF system includes an RF IC device including, transmit components and receive components, at least one low-band transmit interface connected to a first transmit component to output a first signal at a low-band frequency, at least one high-band transmit interface connected to a second transmit component to output a second signal at a high-band frequency, at least one low-band receive interface connected to a first receive component to receive a third signal at the low-band frequency, at least one high-band receive interface connected to a second receive component to receive a fourth signal at the high-band frequency, and mixers connected to upconvert the first signal at the low-band frequency to the second signal at the high-band frequency for transmission from the high-band transmit interface and to downconvert the fourth signal at the high-band frequency received at the high-band receive interface to a fifth signal at the low-band frequency, wherein the upconversion and the downconversion are implemented using a conversion signal at a conversion frequency, and a low-band transmit antenna connected to the at least one low-band transmit interface and tuned to the low-band frequency, a high-band transmit antenna connected to the at least one high-band transmit interface and tuned to the high-band frequency, a low-band receive antenna connected to the at least one low-band receive interface and tuned to the low-band frequency, and a high-band receive antenna connected to the at least one high-band receive interface and tuned to the high-band frequency.

A method for operating an IC device is disclosed. The method involves setting a configuration of the IC device to select from available options of a low-band operational mode and a high-band operational mode, transmitting and receiving RF signals at a low-band frequency when the configuration of the IC device is set to the low-band operational mode, and transmitting and receiving RF signals at a high-band frequency when the configuration of the IC device is set to the high-band operational mode, wherein transmitting RF signals at the high-band frequency comprises upconverting a first signal at the low-band frequency to a second signal at the high-band frequency and wherein receiving RF signals at the high-band frequency comprises downconverting a third signal at the high-band frequency to a fourth signal at the low-band frequency, wherein the upconversion and the downconversion are implemented using a conversion signal at a conversion frequency.

In an embodiment, the method further involves upconverting the first signal at the low-band frequency with an intermediate frequency to output a fifth signal at the low-band frequency plus the intermediate frequency. In an embodiment, the method further involves downconverting the sixth signal at the low-band frequency and the fourth signal at the low-band frequency with the fifth signal at the low-band frequency plus the intermediate frequency to produce seventh signal at the intermediate frequency.

Another embodiment of a method for operating an IC device is disclosed. The method involves setting a configuration of the IC device to select from available options of a low-band operational mode and a high-band operational mode, transmitting and receiving RF signals at a low-band frequency when the configuration of the IC device is set to the low-band operational mode, wherein RF signals are transmitted from a low-band transmit interface of the IC device and wherein RF signals are received at a low-band receive interface of the IC device, and transmitting and receiving RF signals at a high-band frequency when the configuration of the IC device is set to the high-band operational mode, wherein transmitting RF signals at the high-band frequency comprises upconverting a first signal at the low-band frequency to a second signal at the high-band frequency and wherein receiving RF signals at the high-band frequency comprises downconverting a third signal at the high-band frequency to a fourth signal at the low-band frequency, wherein RF signals at the high-band frequency are transmitted from a high-band transmit interface of the IC device and wherein RF signals at the high-band frequency are received at a high-band receive interface of the IC device, and wherein the upconversion and the downconversion are implemented using a conversion signal at a conversion frequency.

A method for operating an RF system is disclosed. The method involves setting a configuration of an IC device to select from available options of a low-band operational mode and a high-band operational mode, transmitting and receiving RF signals at a low-band frequency when the configuration of the IC device is set to the low-band operational mode, wherein RF signals are transmitted from a low-band transmit interface of the IC device and wherein RF signals are received at a low-band receive interface of the IC device, and transmitting and receiving RF signals at a high-band frequency when the configuration of the IC device is set to the high-band operational mode, wherein transmitting RF signals at the high-band frequency comprises upconverting a first signal at the low-band frequency to a second signal at the high-band frequency and wherein receiving RF signals at the high-band frequency comprises downconverting a third signal at the high-band frequency to a fourth signal at the low-band frequency, wherein RF signals at the high-band frequency are transmitted from a high-band transmit interface of the IC device and wherein RF signals at the high-band frequency are received at a high-band receive interface of the IC device, and wherein the upconversion and the downconversion are implemented using a conversion signal at a conversion frequency.

Other aspects in accordance with the invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
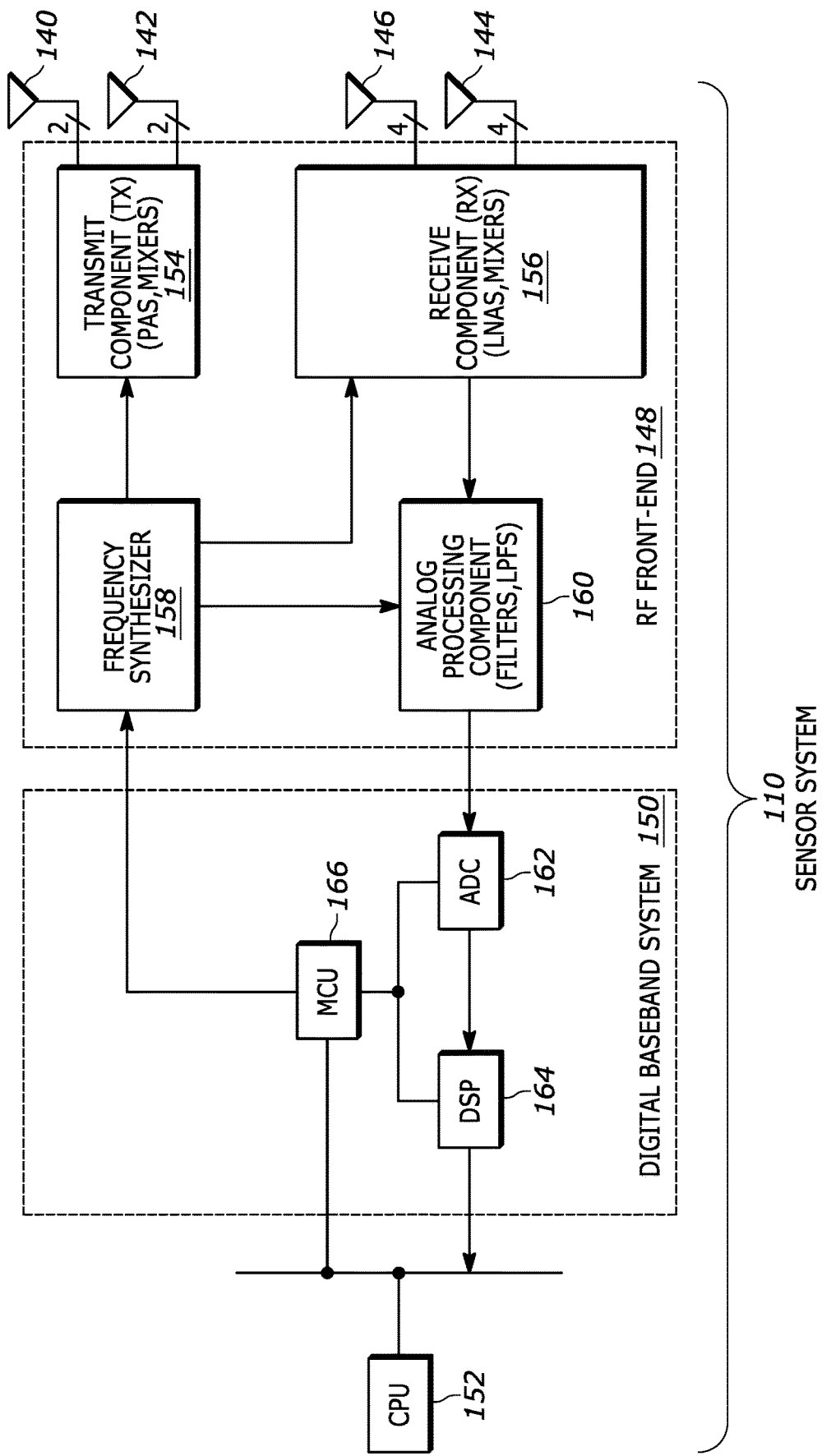
FIG. 1 depicts a functional block diagram of an embodiment of a sensor system that utilizes millimeter range radio waves to monitor a health parameter such as the blood glucose level in a person.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

Radar sensing involves transmitting electromagnetic energy and receiving reflected portions of the transmitted electromagnetic energy. Techniques for transmitting electromagnetic energy in radar systems include impulse, chirp, and stepped frequency techniques. Stepped frequency radar has traditionally been implemented by repeatedly scanning over the same frequency range using the same step size. In accordance with an embodiment of the invention, techniques for radar based sensing involve implementing stepped frequency radar based sensing at a low frequency band and at a high frequency band in a single integrated circuit (IC) device by using a conversion signal to upconvert a low-band transmit signal to a high-band transmit signal and to downconvert a high-band receive signal to a low-band receive signal. Use of a conversion signal to both upconvert and downconvert enables low-band and high-band operational modes to be implemented efficiently on a single IC device. For example, certain radio frequency (RF) components can be used for both low-band and high-band operational modes, thereby making efficient use of valuable IC device real estate. Additionally, the use of a conversion signal enables an efficient multi-step downconversion from both the low-band and the high-band to an intermediate frequency that is desirable for analog-to-digital conversion. In an embodiment, an IC device includes a transmit mixer and a receive mixer that are both fed the same conversion signal in which the transmit mixer upconverts low-band signals to high-band signals for transmission from band-specific antennas and in which the receive mixer downconverts high-band signals received on band-specific antennas to low-band signals that are then further downconverted to an intermediate frequency. In one embodiment, the low-band is in the range of 2-6 GHz, the high-band is in the range of 122-126 GHz, and the conversion signal is at 120 GHz. In another embodiment, the low-band is in the range of 2-6 GHz, the high-band is in the range of 22-26 GHz, and the conversion signal is at 20 GHz. Use of transmit and receive mixers and a conversion signal enables implementation of a highly integrated multi-band RF IC device that can be used to implement a multi-band stepped frequency radar based sensor system. In an embodiment, the stepped frequency radar based sensor system can be used for health parameter monitoring (e.g., blood glucose, heartrate, and/or blood pressure) and in another embodiment, the stepped frequency radar based sensor system can be used in security applications, including, for example, weapon detection.

FIG. 1 depicts a functional block diagram of an embodiment of a sensor system 110 that utilizes RF waves to implement stepped frequency radar sensing that is capable of operating at different frequency bands. The sensor system includes transmit (TX) antennas 140 and 142, receive (RX) antennas 144 and 146, an RF front-end 148, a digital baseband system 150, and a CPU 152. The components of the sensor system may be integrated together in various ways. For example, some combination of components may be fabricated on the same semiconductor substrate and/or included in the same packaged IC device or a combination of packaged IC devices. As described above, in an embodiment, the sensor system is designed to transmit and receive radio waves in at least two distinct frequency bands, such as, for example, a 2-6 GHz frequency band and a 122-126 GHz frequency band. Throughout the description, frequency bands, e.g., the 2-6 GHz and 122-126 GHz frequency bands may also be referred to as frequency ranges or simply as "bands."

In the embodiment of FIG. 1, the sensor system 110 includes two TX antennas 140 and four RX antennas 144 tuned for the 2-6 GHz frequency range (which may be referred to as the "low-band") and two TX antennas 142 and four RX antennas 146 tuned for the 122-126 GHz frequency range (which may be referred to as the "high-band"). Although two TX and four RX antennas are used for each distinct frequency band, in other embodiments there may be another number of antennas, e.g., one or more TX antennas and two or more RX antennas per frequency band. In an embodiment, the antennas are configured to transmit and receive RF waves at the corresponding frequency ranges. For example, the low-band antennas are configured to transmit and receive RF waves in the 2-6 GHz band, e.g., wavelengths in the range of 150-50 mm, and the high-band antennas are configured to transmit and receive RF waves in the 122-126 GHz band, e.g., wavelengths in the range of 2.46-2.38 mm.

In the embodiment of FIG. 1, the RF front-end 148 includes a transmit (TX) component 154, a receive (RX) component 156, a frequency synthesizer 158, and an analogue processing component 160. The transmit component may include elements such as power amplifiers and mixers. The receive component may include elements such as low noise amplifiers (LNAs), variable gain amplifiers (VGAs), and mixers. The frequency synthesizer includes elements to generate electrical signals at frequencies that are used by the transmit and receive components. In an embodiment, the frequency synthesizer may include elements such as an electronic oscillator (e.g., a crystal oscillator), a phase-locked loop (PLL), a frequency multiplier (e.g., a frequency doubler), a frequency divider, and/or a combination thereof. The analogue processing component may include elements such as mixers and filters, e.g., low pass filters (LPFs). Although a certain combination of components is described, the RF front-end may be with other combinations of elements. In an embodiment, components of the RF front-end are implemented in hardware as electronic circuits that are fabricated on the same semiconductor substrate.

The digital baseband system 150 includes an analog-to-digital converter (ADC) 162, a digital signal processor (DSP) 164, and a microcontroller unit (MCU) 166. Although the digital baseband system is shown as including certain elements, the digital baseband system may include some other configuration, including some other combination of elements. The digital baseband system is connected to the CPU 152 via a bus.

Figure 2A:
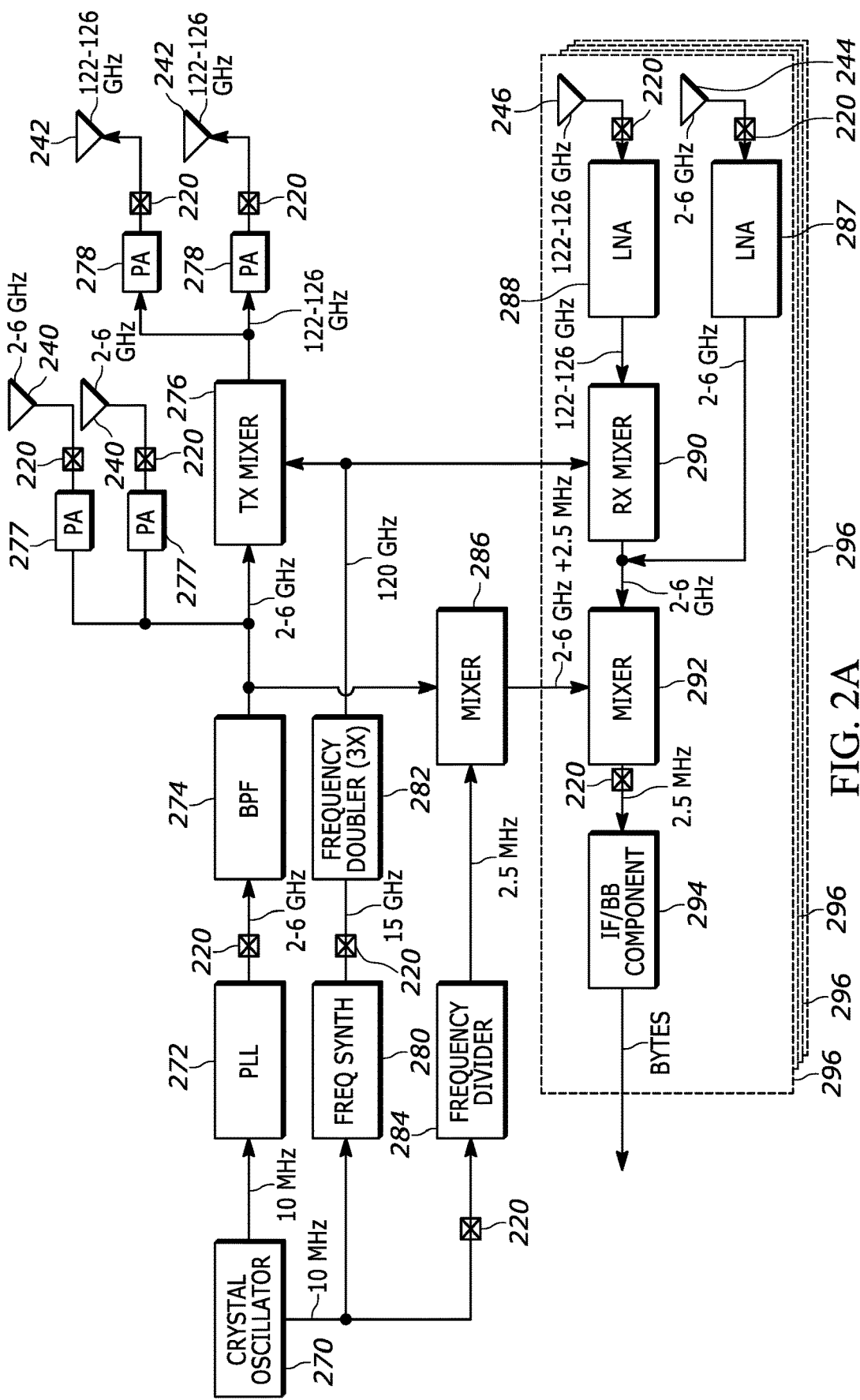
FIG. 2A depicts an expanded view of an embodiment of portions of the sensor system of FIG. 1, including elements of the RF front-end.

FIG. 2A depicts an expanded view of an embodiment of portions of the sensor system 110 of FIG. 1, including various elements of the RF front-end 148. In the embodiment of FIG. 2A, the elements include a crystal oscillator 270, a phase locked loop (PLL) 272, a bandpass filter (BPF) 274, power amplifiers (PAs) 277, TX antennas 240, a mixer 276, power amplifiers (PAs) 278, TX antennas 242, a frequency synthesizer 280, a frequency doubler 282, a frequency divider 284, a mixer 286, an RX antenna 246, a low noise amplifier (LNA) 288, a mixer 290, an RX antenna 244, an LNA 287, a mixer 292, and an Intermediate Frequency/Baseband (IF/BB) component 294. As illustrated in the embodiment of FIG. 2A, the group of receive components identified within the dashed box 296 is repeated four times, e.g., once for each of four distinct receive paths. Although the group of receive components is repeated four times in the embodiment of FIG. 2A, other integer numbers of the group of receive components are possible. For example, it is anticipated that from 1-12 groups of receive components may be included in a single IC device.

The sensor system depicted in FIG. 2A is configured to be able to transmit and receive RF energy at two distinct frequency bands, e.g., a low-band having a frequency range of 2-6 GHz and a high-band having a frequency range of 122-126 GHz. Components that are exclusive to the low-band include the PAs 277 and TX antennas 240, and the RX antennas 244 and LNAs 287. Components that are exclusive to the high-band include the mixer 276 (also referred to as a "TX mixer"), the PAs 278, the TX antennas 242, the RX antennas 246, the LNAs 288, and the mixers 290 (referred to as an "RX mixer"). In an embodiment, the components are "exclusive" to a particular band in that the components are only needed to implement transmit and receive operations in that particular frequency band and are not needed to implement transmit and receive operations in the other band. Additionally, some components are "exclusive" to a particular band because the components have physical characteristics that are designed for the specific frequencies/wavelengths associated with the particular band. For example, it is well known that the physical parameters of antennas are tuned to a particular targeted wavelength and thus antennas that are tuned to a particular targeted wavelength are considered herein to be "exclusive" to that particular wavelength.

In an embodiment, certain components of the system shown in FIG. 2A are fabricated on the same semiconductor substrate. FIG. 2A depicts interfaces 220 that represent physical interfaces of an IC device. For example, the interfaces included are conductive pads that enable electrical connection to other components as is known in the field. In the embodiment of FIG. 2A, the components positioned between at least two interfaces are included on the IC device. In particular, the components BPF 274, PAs 277, TX mixer 276, PAs 278, frequency doubler 282, mixer 286, LNAs 287, LNAs 288, RX mixers 290, and mixer 292 are included on a single IC device, e.g., on the same semiconductor substrate of a packaged IC device. The interfaces 220 provide a way to electrically connect the components of the IC device to other components of the sensor system as is known in the field.

Figure 2B:
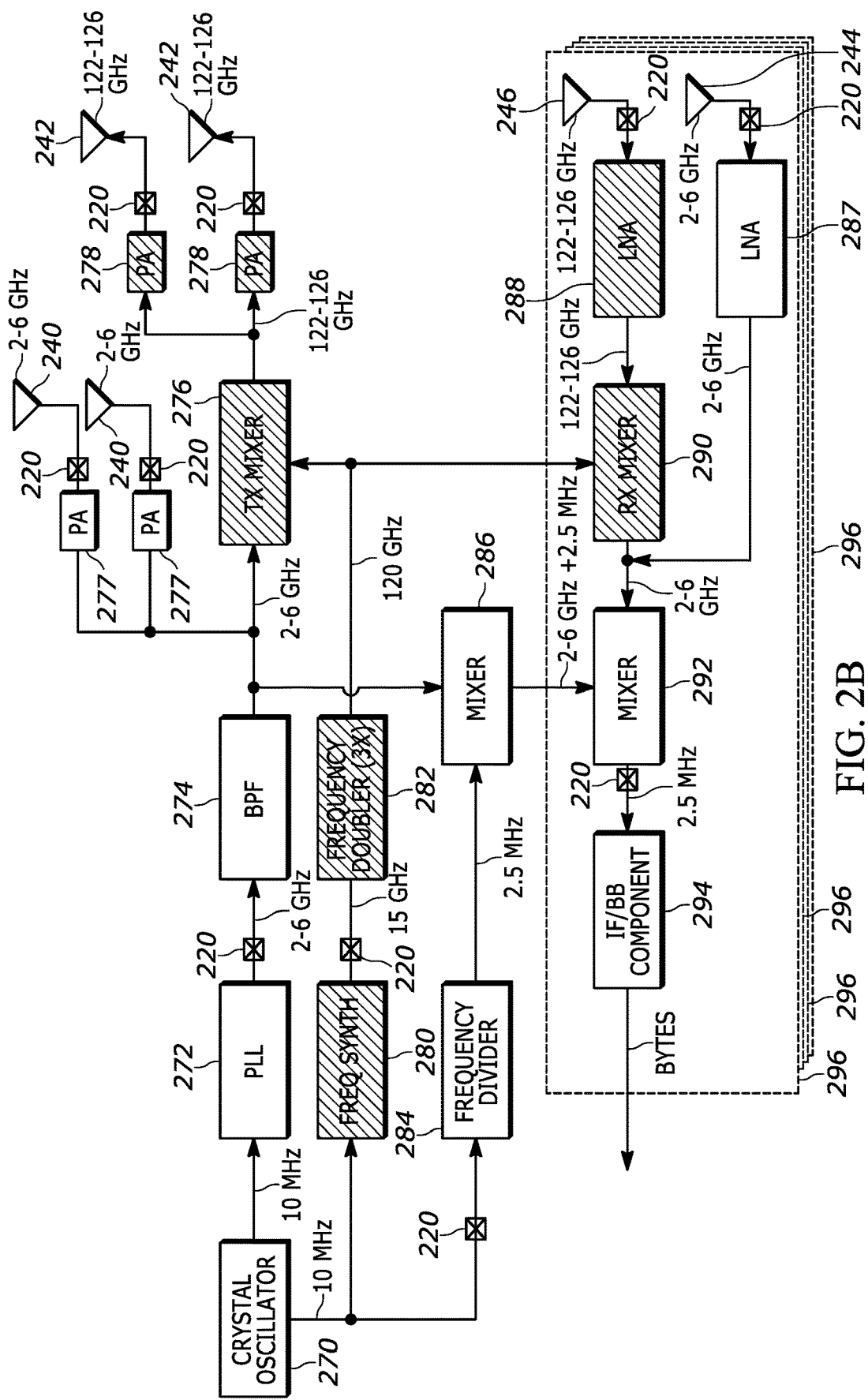
FIG. 2B illustrates the sensor system of FIG. 2A in a low-band operational mode.
Figure 2C:
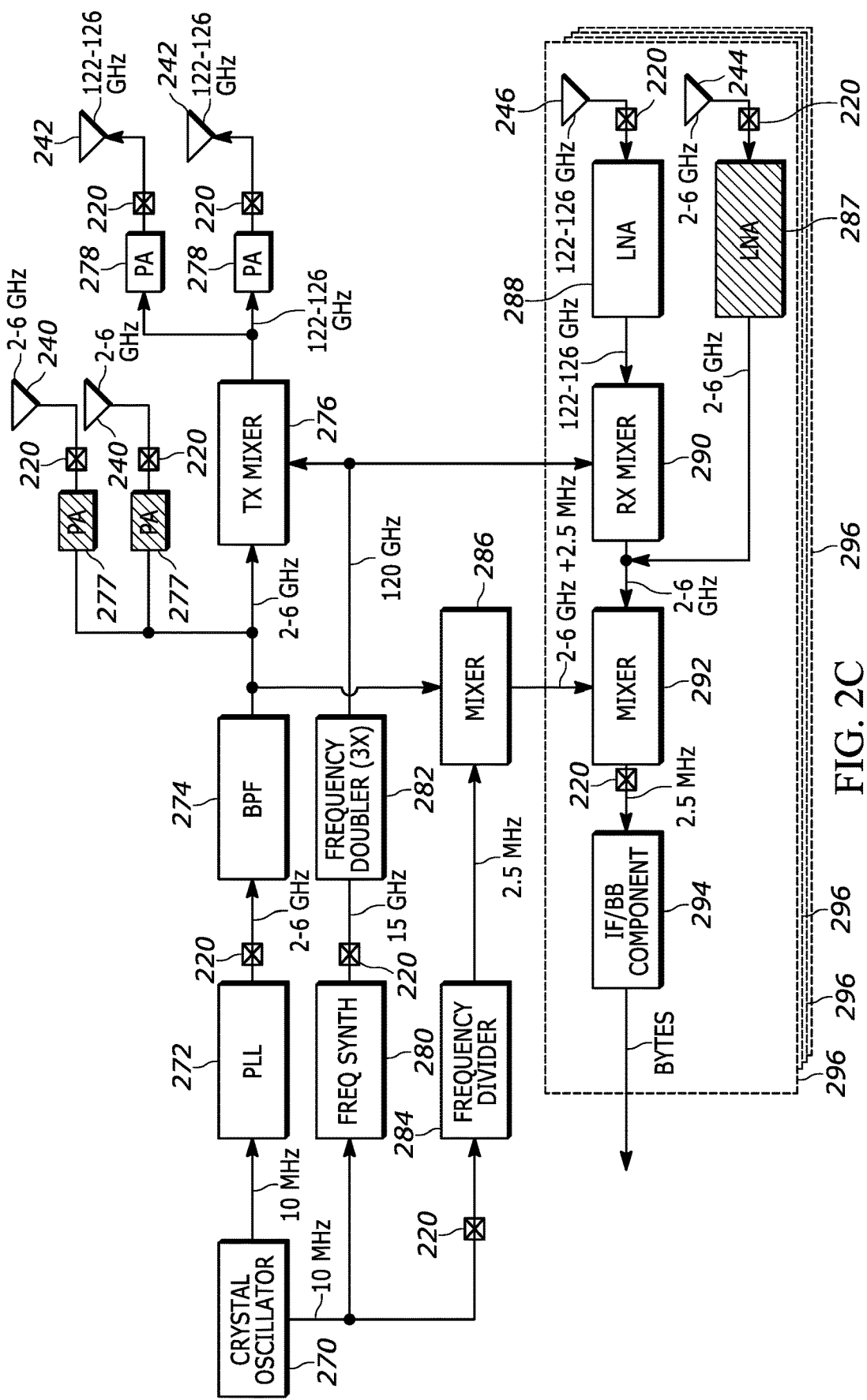
FIG. 2C illustrates the sensor system of FIG. 2A in a high-band operational mode.

As described above, the sensor system is a multi-band sensor system that is configured to implement stepped frequency radar-based sensing in at least two distinct frequency bands, e.g., a 2-6 GHz band and a 122-126 GHz band. Operational modes of the multi-band sensor system shown in FIG. 2A are described with reference to FIGS. 2B and 2C. In particular, a low-band operational mode (including transmit and receive operations at 2-6 GHz) is described with reference to FIG. 2B and a high-band operational mode (including transmit and receive operations at 122-126 GHz) is described with reference to FIG. 2C. With reference to FIGS. 2B and 2C, description of a transmit operation generally corresponds to a left-to-right progression and description of a receive operation generally corresponds to a right-to-left progression. Additionally, components that are not needed in the respective low-band and high-band operational modes are identified with cross hatching. In an embodiment, components that are not needed in a particular operational mode may be powered down, powered off, and/or power gated to conserve power. For example, in the low-band operational mode illustrated in FIG. 2B, the frequency synthesizer 280, the frequency doubler 282, the TX mixer 276, the PAs 278, the LNAs 288, and the RX mixers 290 can be powered down as indicated by the cross hatching. Likewise, in the high-band operational mode illustrated in FIG. 2C, the PAs 277 and the LNAs 287 can be powered down as indicated by the cross hatching.

With reference to FIG. 2B and with regard to a low-band transmit operation, the crystal oscillator 270 generates an analog signal (e.g., a base signal) at a base frequency of, for example, 10 MHz. The 10 MHz signal is provided to the PLL 272 and the PLL uses the 10 MHz signal to generate an analog signal that is in the 2-6 GHz frequency range. The 2-6 GHz signal is provided to the BPF 274 of the IC device via corresponding interface 220 and the BPF filters the input signal and passes a signal in the 2-6 GHz range to the PAs 277. RF signals in the 2-6 GHz range are provided from the PAs 277 to the TX antennas 240 via corresponding interfaces 220 and then transmitted as radio waves from the antennas. In an embodiment, the 2-6 GHz signals are output at 20 dBm (decibels (dB) with reference to 1 milliwatt (mW)). In an embodiment and as described below, the PLL is controlled to generate discrete frequency pulses between 2-6 GHz that are used for stepped frequency transmission.

The 2-6 GHz signal from the BPF 274 is also provided to the mixer 286. The 10 MHz base signal from the crystal oscillator 270 is also provided via corresponding interface 220 to the frequency divider 284, which divides the frequency down, e.g., from 10 MHz to 2.5 MHz via, for example, two divide-by-two operations, and provides an output signal at 2.5 MHz to the mixer 286. In an embodiment, the 2.5 MHz signal is referred to as an "intermediate frequency" or "IF" signal. The mixer 286 also receives the 2-6 GHz signal from the BPF 274 and upconverts the 2-6 GHz signal to provide a signal at 2-6 GHz+2.5 MHz to the mixer 292 for receive signal processing.

With reference to a receive operation, electromagnetic (EM) energy is received at the RX antenna 244 (e.g., one of four RX antennas) and converted to electrical signals, e.g., voltage and current. For example, electromagnetic energy in the 2-6 GHz frequency band is converted to an electrical signal that corresponds in magnitude (e.g., power in dBm), frequency (e.g., GHz), and phase to the electromagnetic energy that is received at the RX antenna. The electrical signal is provided to the LNA 287 via corresponding interface 220. In an embodiment, the LNA 287 amplifies signals in the 2-6 GHz frequency range and outputs an amplified 2-6 GHz signal. The amplified 2-6 GHz signal is then mixed (e.g., downconverted) with the 2-6 GHz+2.5 MHz signal at mixer 292 to generate a 2.5 MHz signal ("IF" signal) that corresponds to the electromagnetic energy that was received at the RX antenna. For example, when a 2 GHz signal is being transmitted from the TX antennas 240 and received at the RX antenna 244, the mixer 292 receives a 2 GHz signal that corresponds to the electromagnetic energy that was received at the RX antenna 244 and a 2 GHz+2.5 MHz signal from the mixer 286. The mixer 292 mixes (e.g., downconverts) the 2 GHz signal that corresponds to the electromagnetic energy that was received at the RX antenna 244 with the 2 GHz+2.5 MHz signal from the mixer 286 to generate a 2.5 MHz signal ("IF" signal) that corresponds to the electromagnetic energy that was received at the RX antenna 244. The 2.5 MHz signal that corresponds to the electromagnetic energy that was received at the RX antenna 244 is provided to the IF/BB component 294 via corresponding interface 220 for analog-to-digital conversion. The above-described receive process can be implemented in parallel on each of the four receive paths 296. As mentioned above and as indicated by the cross-hatching, the frequency synthesizer 280, frequency doubler 282, TX mixer 276, and RX mixer 290 are not needed to implement the low-band operational mode of the multi-band sensor system and thus may be, for example, powered down, powered off, or power gated, to conserve power.

With reference to FIG. 2C and with regard to a high-band transmit operation, the crystal oscillator 270 generates an analog signal at a frequency of 10 MHz. The 10 MHz signal is provided to the PLL 272, to the frequency synthesizer 280, and to the frequency divider 284. The PLL uses the 10 MHz signal to generate an analog signal that is in the 2-6 GHz frequency range. The 2-6 GHz signal is provided to the BPF 274 via corresponding interface 220, which filters the input signal and passes a signal in the 2-6 GHz range to the mixer 276. The 2-6 GHz signal is also provided to the mixer 286.

Dropping down in FIG. 2C, the 10 MHz signal is used by the frequency synthesizer 280 to produce a 15 GHz signal (also referred to as a "pre-conversion" signal). The 15 GHz signal is provided to the frequency doubler 282 via corresponding interface 220 and is used by the frequency doubler 282 to generate a signal (also referred to as a "conversion" signal) at 120 GHz (also referred to as the "conversion" frequency). In an embodiment, the frequency doubler 282 includes a series of three frequency multipliers that each double the frequency, e.g., from 15 GHz to 30 GHz, and then from 30 GHz to 60 GHz, and then from 60 GHz to 120 GHz. As is described below, the 120 GHz conversion signal is used to upconvert transmit signals and to downconvert receive signals to efficiently implement the high-band operational mode. Once generated, the 120 GHz conversion signal and the 2-6 GHz signal are provided to the mixer 276 (e.g., the TX mixer), which mixes (e.g., upconverts) the two signals to generate a signal at 122-126 GHz depending on the frequency of the 2-6 GHz signal. The 122-126 GHz signal output from the mixer 276 is provided to the power amplifiers 278. RF signals in the 122-126 GHz range are then provided to the TX antennas 242 via corresponding interfaces 220 and transmitted from the antennas as radio waves. In an embodiment, the 122-126 GHz signals are output at 15 dBm (decibels (dB) with reference to 1 milliwatt (mW)). In an embodiment and as described below, the PLL 272 is controlled to generate discrete frequency pulses between 2-6 GHz that are used for stepped frequency transmission and therefore, the particular frequency of the 122-126 GHz signal varies in time in lock step with the 2-6 GHz signal.

The 10 MHz signal from the crystal oscillator 270 is also provided to the frequency divider 284 via corresponding interface 220, which divides the frequency down, e.g., from 10 MHz to 2.5 MHz via, for example, two divide-by-two operations, and provides an output signal at 2.5 MHz to the mixer 286. The mixer 286 also receives the 2-6 GHz signal from the BPF 274 and upconverts the 2-6 GHz signal to provide a signal at 2-6 GHz+2.5 MHz to the mixer 292 for receive signal processing.

With reference to a receive operation, electromagnetic (EM) energy is received at the RX antenna 246 and converted to electrical signals, e.g., voltage and current. For example, electromagnetic energy in the 122-126 GHz frequency band is converted to an electrical signal that corresponds in magnitude (e.g., power in dBm), frequency (e.g., GHz), and phase to the electromagnetic energy that is received at the RX antenna 246. The electrical signal is provided to the LNA 288 via corresponding interface 220. In an embodiment, the LNA 288 amplifies signals in the 122-126 GHz frequency range and outputs an amplified 122-126 GHz signal. The amplified 122-126 GHz signal is provided to the RX mixer 290, which mixes (e.g., down-converts) the received 122-126 GHz signal with the 120 GHz conversion signal from the frequency doubler 282 to generate a 2-6 GHz signal that corresponds to the electromagnetic energy that was received at the RX antenna 246. The resulting 2-6 GHz signal is then mixed with the 2-6 GHz+2.5 MHz signal at mixer 292 to generate a 2.5 MHz signal ("IF" signal) that corresponds to the electromagnetic energy that was received at the RX antenna 246. For example, when a 122 GHz signal is being transmitted from the TX antennas 242 and received at the RX antenna 246, the mixer 292 receives a 2 GHz signal that corresponds to the electromagnetic energy that was received at the antenna and the 2 GHz+2.5 MHz signal from the mixer 286. The mixer 292 mixes the 2 GHz signal that corresponds to the electromagnetic energy that was received at the RX antenna with the 2 GHz+2.5 MHz signal from the mixer 286 to generate a 2.5 MHz signal that corresponds to the electromagnetic energy that was received at the RX antenna 246. The 2.5 MHz signal that corresponds to the electromagnetic energy that was received at the RX antenna 246 is provided to the IF/BB component 294 via corresponding interface 220 for analog-to-digital conversion. The above-described receive process can be implemented in parallel on each of the four receive paths 296. As mentioned above and as indicated by the cross-hatching, the PAs 277 and LNAs 287 are not needed to implement the low-band operational mode of the multi-band sensor system and thus may be, for example, powered down, powered off, or power gated, to conserve power. The multiple mixers and corresponding mixing operations as described herein implement a "compound mixing" architecture that enables use of such high frequencies, such as the 122-126 GHz frequency range.

As described above with reference to FIG. 2C, the same 120 GHz conversion signal is used to both upconvert transmit signals and downconvert receive signals. In particular, the 120 GHz conversion signal is used to upconvert the 2-6 GHz signal to a 122-126 GHz signal for transmission and the same 120 GHz conversion signal is used to downconvert a 122-126 GHz that is received on a receive antenna to a 2-6 GHz signal. Thus, the frequency synthesizer 280 and the frequency doubler 282 are used for both transmit and receive operations.

In an embodiment, the operational mode of the sensor system is set by a user by inputting a mode selection command. In other embodiments, the operational mode is set by mode selection logic that is embedded into the system, such as mode selection logic that is embedded into the DSP 164, the MCU 166, and/or the CPU 152. In an embodiment, once an operational mode is selected, components of the sensor system are configured such that the system operates in either a low-band operational mode or a high-band operational mode as described above with reference to FIGS. 2A-2C. In an embodiment, setting a configuration of the IC device comprises powering up/down certain components as described with reference to FIGS. 2A-2C. Additionally, setting a configuration of the IC device may comprise setting the configuration of a switch (e.g., switch 583 in FIG. 5) to switch between different conversion signals. Additionally, although not shown in FIGS. 2A-2C, the sensor system may include other switches, whose configuration can be set, that control how signals are distributed amongst the components. In an embodiment, the low-band and high-band operational modes are both available operational mode options.

The system described with reference to FIGS. 2A-2C can be used to generate, transmit, and receive various discrete frequencies that can be used to implement, for example, stepped frequency radar detection. As described above, multiple mixing operations are performed to implement a sensor system at such a high frequency, e.g., in the 122-126 GHz range. Additionally, many of the components of the multi-band system are used to implement both the low-band and the high-band operational modes. In particular, the crystal oscillator 270, the PLL 272, the BPF 274, the frequency divider 280, the mixer 286, the mixer 292, and the IF/BB component 294 are used for both the low-band and the high-band operational modes. Using the crystal oscillator 270, the PLL 272, the BPF 274, the frequency divider 280, the mixer 286, and the mixer 292 for both operational modes of the multi-band sensor system makes efficient use of RF components and conserves valuable real estate on the semiconductor substrate. Additionally, the two-step frequency conversion implemented by the mixers 286 and 292 enables the use of an intermediate frequency at, for example, 2.5 MHz, which is desirable for analog-to-digital conversion at the IF/BB component 294.

Figure 3:
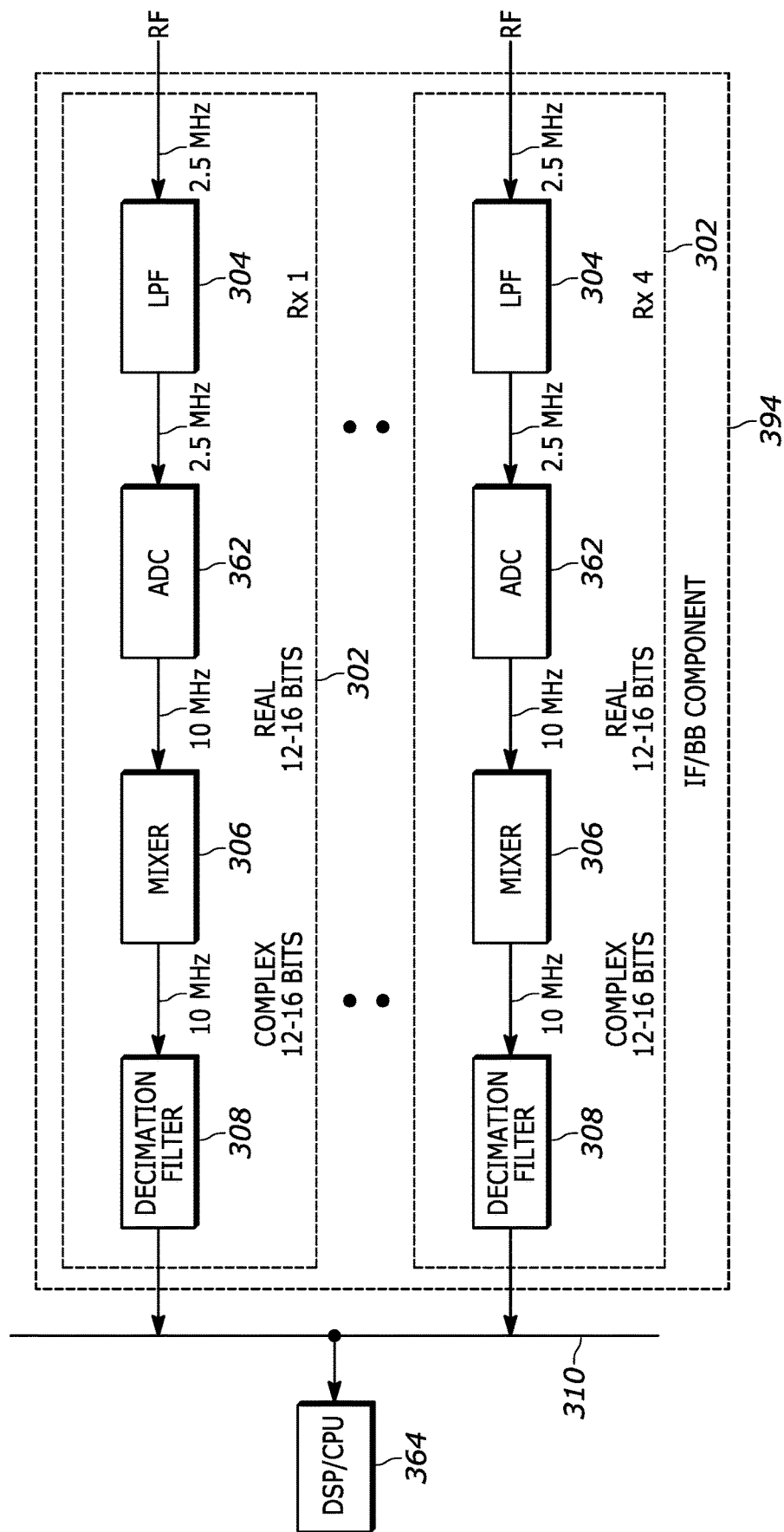
FIG. 3 depicts an embodiment of the IF/BB component shown in FIG. 6.

FIG. 3 depicts an embodiment of the IF/BB component 394 shown in FIGS. 2A-2C. The IF/BB component 394 of FIG. 3 includes similar signal paths 302 for each of the four receive paths/RX antennas and each signal path includes a low pass filter (LPF) 304, an analog-to-digital converter (ADC) 362, a mixer 306, and a decimation filter 308. The operation of receive path 1, RX1, is described.

As described above with reference to FIGS. 2A-2C, the 2.5 MHz signal (IF signal) from mixer 292 (FIG. 2A) is provided to the IF/BB component 294/394, in particular, to the LPF 304 of the IF/BB component 394. In an embodiment, the LPF filters the 2.5 MHz signal to remove the negative frequency spectrum and noise outside of the desired bandwidth. After passing through the LPF, the 2.5 MHz signal is provided to the ADC 362, which converts the 2.5 MHz signal (e.g., IF signal) to digital data at a sampling rate of 10 MHz (e.g., as 12-16 bits of "real" data). The mixer 306 multiplies the digital data with a complex vector to generate a digital signal (e.g., 12-16 bits of "complex" data), which is also sampled at 10 MHz. Although the signal is sampled at 10 MHz, other sampling rates are possible, e.g., 20 MHz. The digital data sampled at 10 MHz is provided to the decimation filter, which is used to reduce the amount of data by selectively discarding a portion of the sampled data. For example, the decimation filter reduces the amount of data by reducing the sampling rate and getting rid of a certain percentage of the samples, such that fewer samples are retained. The reduction in sample retention can be represented by a decimation factor, M, and may be, for example, about 10 or 100 depending on the application, where M equals the input sample rate divided by the output sample rate.

The output of the decimation filter 306 is digital data that is representative of the electromagnetic energy that was received at the corresponding RX antenna. In an embodiment, samples are output from the IF/BB component 394 at rate of 1 MHz (using a decimation factor of 10) or at a rate of 100 kHz (using a decimation factor of 100). The digital data is provided to a DSP and/or CPU 364 via a bus 310 for further processing. For example, the digital data is processed to isolate a signal from a particular location, e.g., to isolate signals that correspond to electromagnetic energy that was reflected from a certain physical location. In an embodiment, signal processing techniques are applied to implement beamforming, Doppler effect processing, and/or leakage mitigation to isolate a desired signal from other undesired signals.

In conventional RF systems, the analog-to-digital conversion process involves a high direct current (DC), such that the I ("real") and Q ("complex") components of the RF signal at DC are lost at the ADC. Using the multi-band system as described above with reference to FIGS. 1-3, the intermediate IF is not baseband, so I and Q can be obtained after analog-to-digital conversion and digital mixing as shown in FIG. 3.

In an embodiment, digital signal processing of the received signals may involve implementing Kalman filters to smooth out noisy data. In another embodiment, digital signal processing of the received signals may involve combining receive chains digitally. Other digital signal processing may be used to implement beamforming, Doppler effect processing, and ranging. Digital signal processing may be implemented in a DSP and/or in a CPU.

Figure 4:
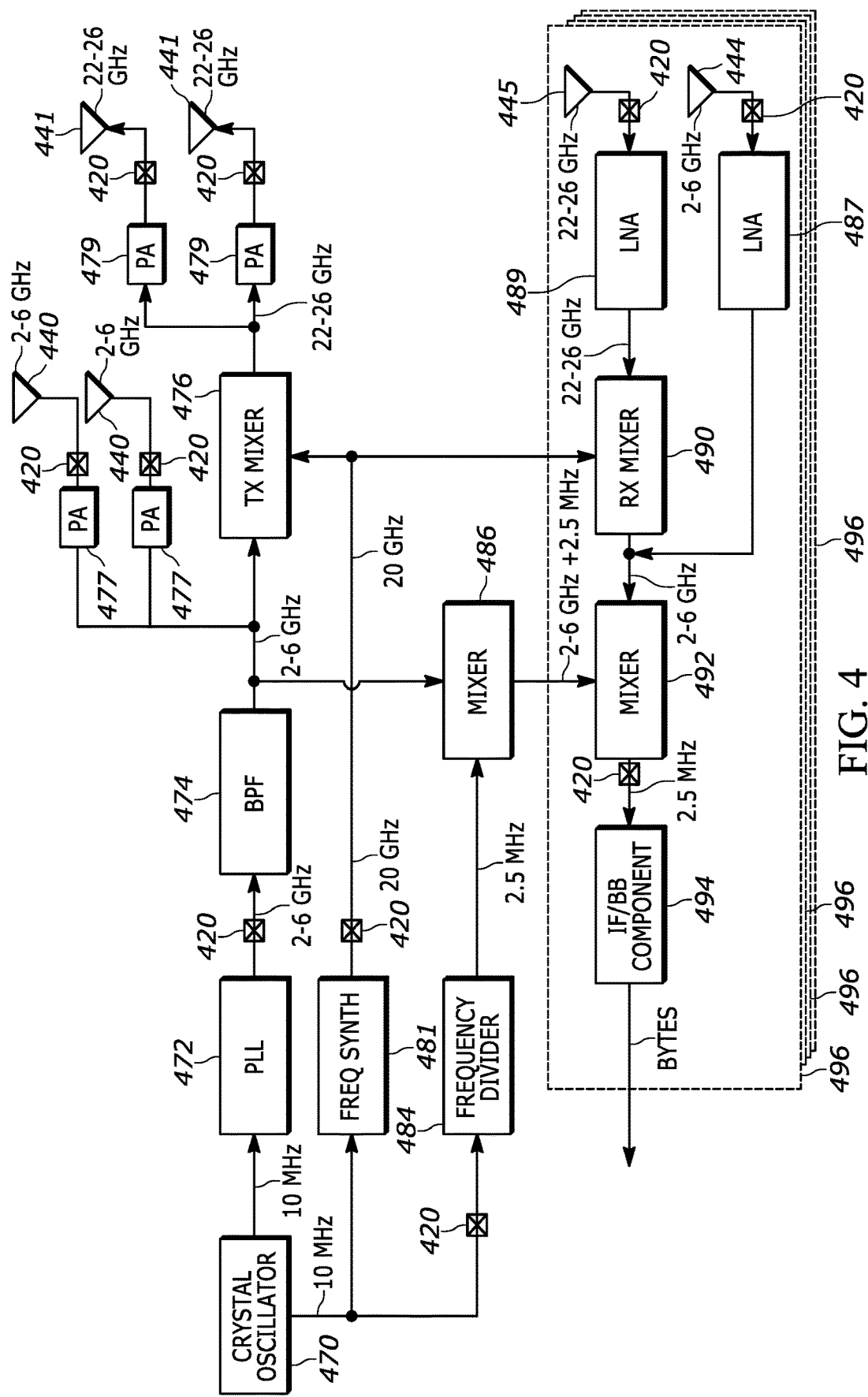
FIG. 4 depicts an embodiment of a multi-band sensor system that is configured to transmit and receive RF energy at a low-band of 2-6 GHz and at a high-band of 22-26 GHz.

The multi-band sensor system is described above as having a low-band at 2-6 GHz and a high-band at 122-126 GHz. Although a particular combination of two distinct bands is described above, other combinations of distinct bands are possible. For example, the sensor system depicted in FIG. 4 is configured to transmit and receive RF energy at a low-band of 2-6 GHz and at a high-band of 22-26 GHz. The components and operation of the system shown in FIG. 4 are similar to the components and operation as described above with reference to FIGS. 2A-2C with a few differences. With reference to FIG. 4, the frequency synthesizer 481 is configured to generate a conversion signal at 20 GHz from the 10 MHz base signal. The 20 GHz conversion signal is provided to the TX mixer 476 and to the RX mixer 490 for upconversion and downconversion, respectively. Additionally, the high-band PAs 479, TX antennas 441, RX antennas 445, and LNAs 489 are configured for 22-26 GHz RF signals. In particular, the TX antennas 441 and RX antennas 445 are configured to transmit and receive, respectively, RF waves in the 22-26 GHz frequency range, e.g., at wavelengths in a range of 13.6-11.5 mm. As with the embodiment described with reference to FIGS. 2A-2C, some of the components are used to implement both the low-band and the high-band operational modes. In particular, the crystal oscillator 470, the PLL 472, the BPF 474, the frequency divider 484, the mixer 486, the mixer 492, and the IF/BB component 494 are used for both the low-band and the high-band operational modes.

Figure 5:
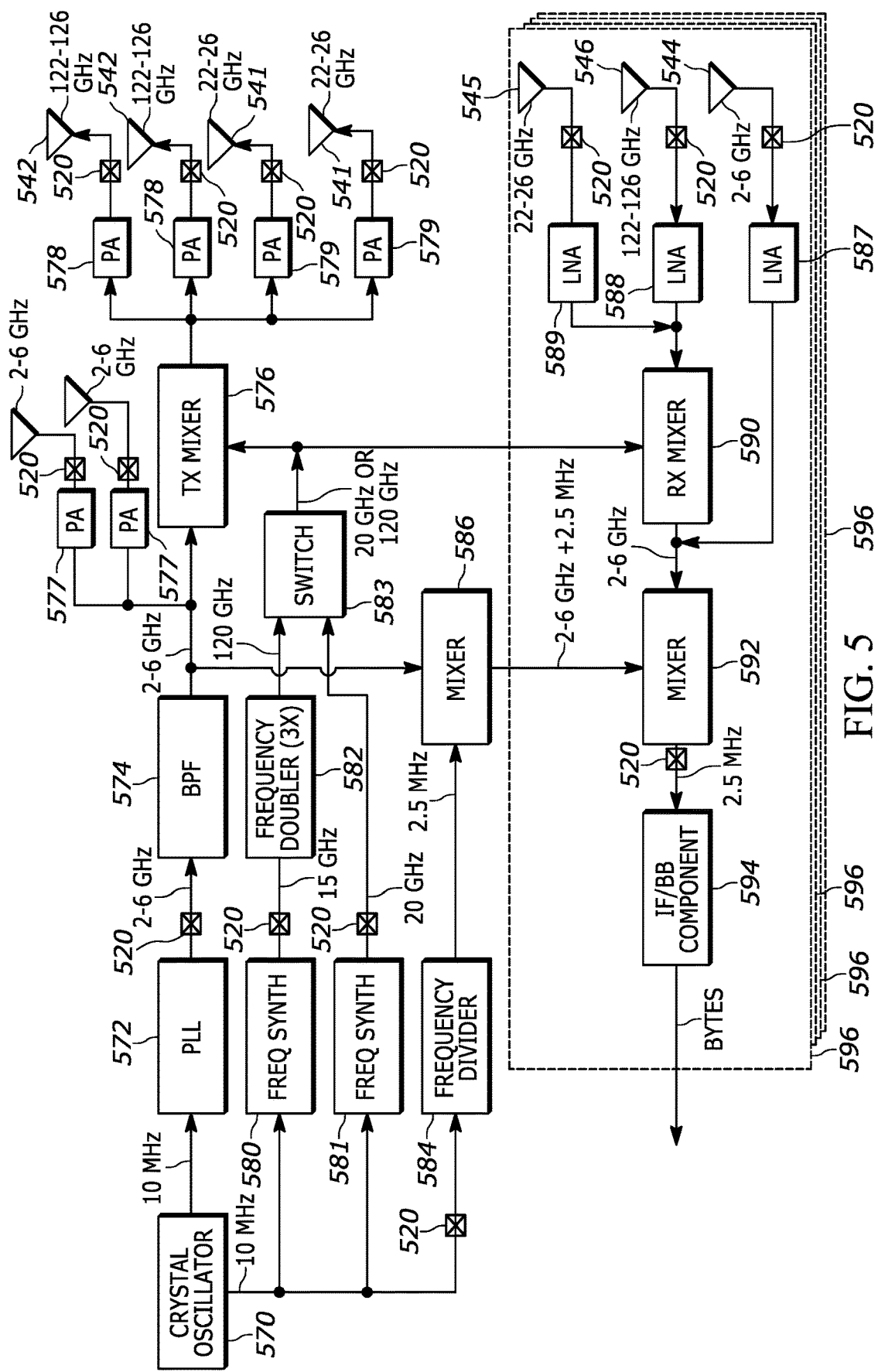
FIG. 5 depicts an embodiment of a multi-band sensor system that is configured to transmit and receive RF energy at a low-band of 2-6 GHz, at a medium-band of 22-26 GHz, and at a high-band of 122-126 GHz

The multi-band sensor systems described with reference to FIGS. 2A-2C and FIG. 4 are configured for two distinct bands, a low-band at 2-6 GHz and a high-band at 122-126 GHz or 22-26 GHz. FIG. 5 depicts an embodiment of a multi-band system that is configured to operate at three distinct bands. In particular, the sensor system of FIG. 5 is configured to operate at a low-band of 2-6 GHz, a medium-band of 22-26 GHz, and a high-band of 122-126 GHz. The components and operation of the system shown in FIG. 5 are similar to the components and operation as described above with reference to FIGS. 2A-2C and FIG. 4 with a few differences. With reference to FIG. 5, the sensor system includes all of the components of FIGS. 2A-2C along with an additional frequency synthesizer 581 that is configured to generate a conversion signal at 20 GHz from the 10 MHz base signal and a switch 583 configured to select between the 20 GHz conversion signal and the 120 GHz conversion signal depending on which one of the three available operational modes of the sensor system is selected. When the system is in an operational mode for the 22-26 GHz band (e.g., the "medium-band"), the switch 583 is configured such that the 20 GHz conversion signal is provided to the TX mixer 576 for upconversion and to the RX mixer 590 for downconversion and when the system is in an operational mode for the 122-126 GHz band (e.g., the "high-band"), the switch 583 is configured such that the 120 GHz conversion signal is provided to the TX mixer 576 for upconversion and to and the RX mixer 590 for downconversion. Additionally, the medium-band PAs 579, TX antennas 541, RX antennas 545, and LNAs 589 are configured for 22-26 GHz RF signals. For example, the TX antennas 541 and RX antennas 545 are configured to transmit and receive, respectively, RF waves in the 22-26 GHz frequency range, e.g., wavelengths in the range of 13.6-11.5 mm. As with the embodiment described with reference to FIGS. 2A-2C, some of the components are used to implement operations at all three bands. In particular, the crystal oscillator 570, the PLL 572, the BPF 574, the frequency divider 584, the mixer 586, the mixer 582, and the IF/BB component 594 are used for all three operational modes, e.g., the low-band, the medium-band, and the high-band operational modes. The use of certain components for multi-band operation can save precious real estate on an IC device to reduce the size of the IC device and/or to leave room for other components to be integrated onto the same IC device.

Although examples of conversion signals at 120 GHz and 20 GHz are described herein, conversion signals at other frequencies are possible. As described herein, the frequency of the conversion signal sets the "distance" (e.g., in terms of frequency separation) between the distinct bands. Thus, the distance between the distinct bands of a multi-band sensor system can be controlled by controlling the frequency of the conversion signal. In an embodiment, a multi-band sensor system that has operational modes in more than three distinct bands can be implemented. For example, a multi-band sensor system that has operational modes in more than three distinct bands can be implemented by adding additional conversion frequencies and a switching mechanism to select the desired conversion frequency from available options of conversion frequencies. Although operation of the multi-band sensor system is described as transmitting and receiving RF energy at one band at a time, it is also possible that RF energy could be generated at multiple different bands and transmitted simultaneously from the respective band-specific TX antennas and then received in, for example, a time-division-multiplex (TDM) manner on the receive side. For example, if RF energy at three different bands is transmitted simultaneously, a switching mechanism could be used on the receive side of the system to rotate between selecting one of the three bands to provide band-specific signals to the mixer 592 (FIG. 5).

In an embodiment, certain components of the sensor system are integrated onto a single semiconductor substrate and/or onto a single packaged IC device (e.g., a packaged IC device that includes multiple different semiconductor substrates (e.g., different die) and antennas). For example, elements such as the components of the RF front-end 148, and/or components of the digital baseband system 150 (FIGS. 1-3) are integrated onto the same semiconductor substrate (e.g., the same die). In an embodiment, components of the multi-band sensor system are integrated onto a single semiconductor substrate that is approximately 5 mm×5 mm. In an embodiment, the semiconductor substrate and the packaged IC device includes interfaces for exchanging electrical signals with other components such as a DSP, a CPU, and/or a bus. In some embodiments, the packaged IC device may include the DSP and/or CPU or the packaged IC device may include some DSP and/or CPU functionality.

Because the multi-band sensor system includes operational modes at distinctly different frequency bands, e.g., 2-6 GHz, 22-24 GHz, and 122-126 GHz, the transmit and receive antenna configurations needed to support the distinct bands are physical different. As such, antennas tuned for the 2-6 GHz band may not provide acceptable performance in the 22-26 GHz band or in the 122-126 GHz band. Likewise, antennas tuned for the 122-126 GHz band may not provide acceptable performance in the 2-6 GHz band or in the 22-26 GHz band and antennas tuned for the 22-26 GHz band may not provide acceptable performance in the 2-6 GHz band or in the 122-126 GHz band. Thus, it is desirable that the multi-band sensor system utilize band-specific antennas that are connected to the RF IC device by band-specific interfaces. In an embodiment, the band-specific configurations of the antennas involve antenna dimensions that correspond to the wavelengths of the particular band. Although the RF IC devices described herein include band-specific interfaces, the utilization of conversion mixers (e.g., upconversion and downconversion mixers) provides for efficient usage of RF components even in light of the band-specific antennas requirements.

Figure 6:
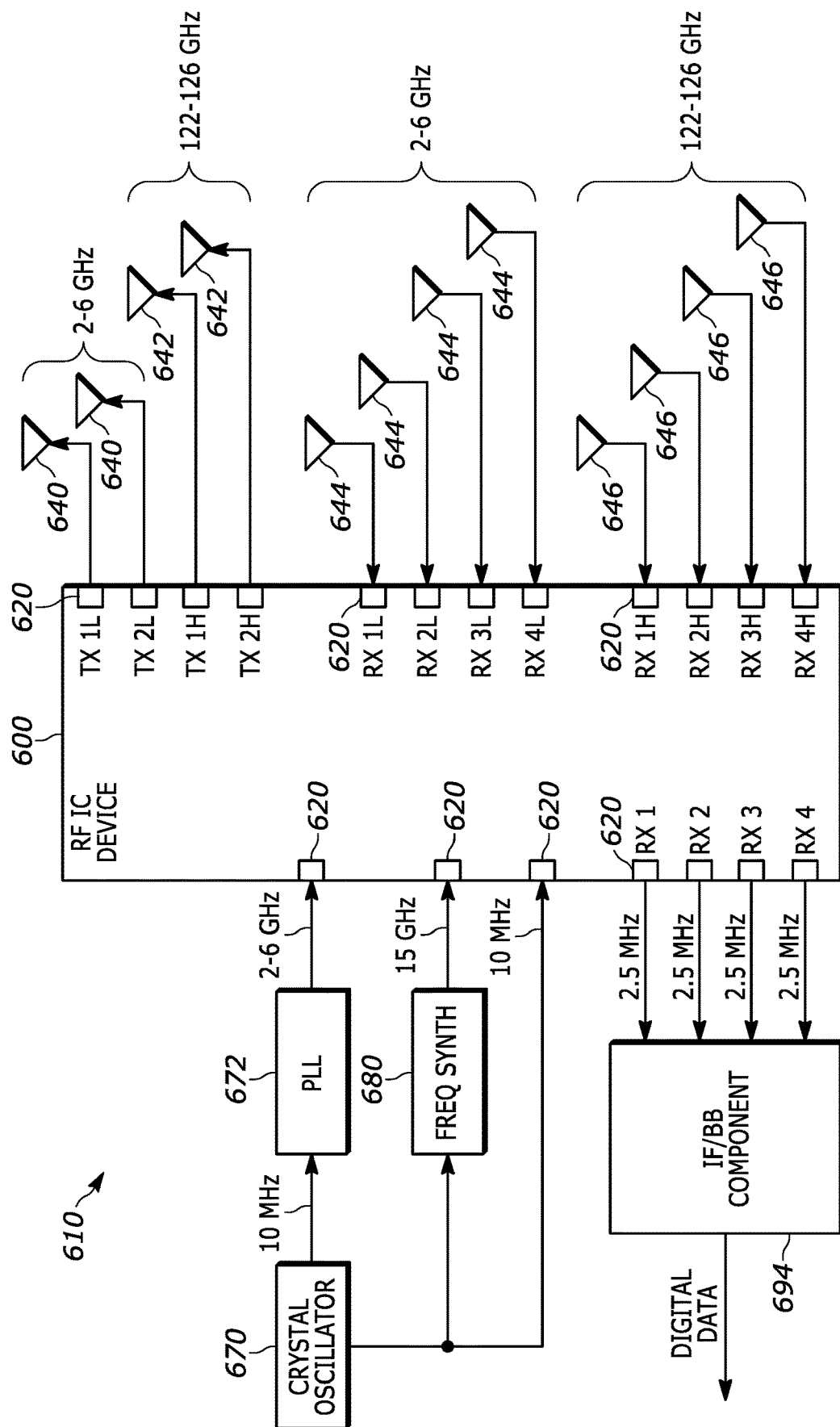
FIG. 6 depicts an embodiment of a multi-band sensor system in which components of the RF-front end are incorporated into a single RF IC device.

In an embodiment, various components of a multi-band sensor system are integrated into a single RF IC device. FIG. 6 depicts an embodiment of a multi-band sensor system 610 in which components of the RF front-end are incorporated into a single RF IC device 600. FIG. 6 is provided in part to more clearly illustrate how a single IC device is integrated with other components of a multi-band sensor system. As shown in FIG. 6, the RF IC device 600 includes various signal interfaces 620, including a signal interface for a 2-6 GHz signal, a signal interface for a 15 GHz signal (e.g., a pre-conversion signal), a signal interface for a 10 MHz signal (a base signal), two low-band TX antenna interfaces (TX 1L and TX 2L), two high-band TX antenna interfaces (TX 1H and TX 2H), four low-band RX antenna interfaces (RX 1L, RX 2L, RX 3L, and RX 4L), four high-band RX antenna interfaces (RX 1H, RX 2H, RX 3H, and RX 4H), and four IF/BB interfaces (RX 1, RX 2, RX 3, and RX 4). The interfaces 620 shown in FIG. 6 corresponds to the interfaces 220 shown in FIGS. 2A-2C and the components within the RF IC device, which are not shown in FIG. 6, correspond to the components described with reference to FIGS. 2A-2C as being on the same IC device, e.g., fabricated into the same semiconductor substrate. In an embodiment, the RF IC device 600 includes additional interfaces for operational control (e.g., setting the configuration of the system to select the operational mode from available operational modes) and power (e.g., power supply and ground). In the embodiment of FIG. 6, components connected to the RF IC device 600 via the interfaces 620 include a crystal oscillator 670, a PLL 672, a frequency synthesizer 680, an IF/BB component 694, low-band TX antennas 640, high-band TX antennas 642, low-band RX antennas 644, and high-band RX antennas 646.

Figure 7:
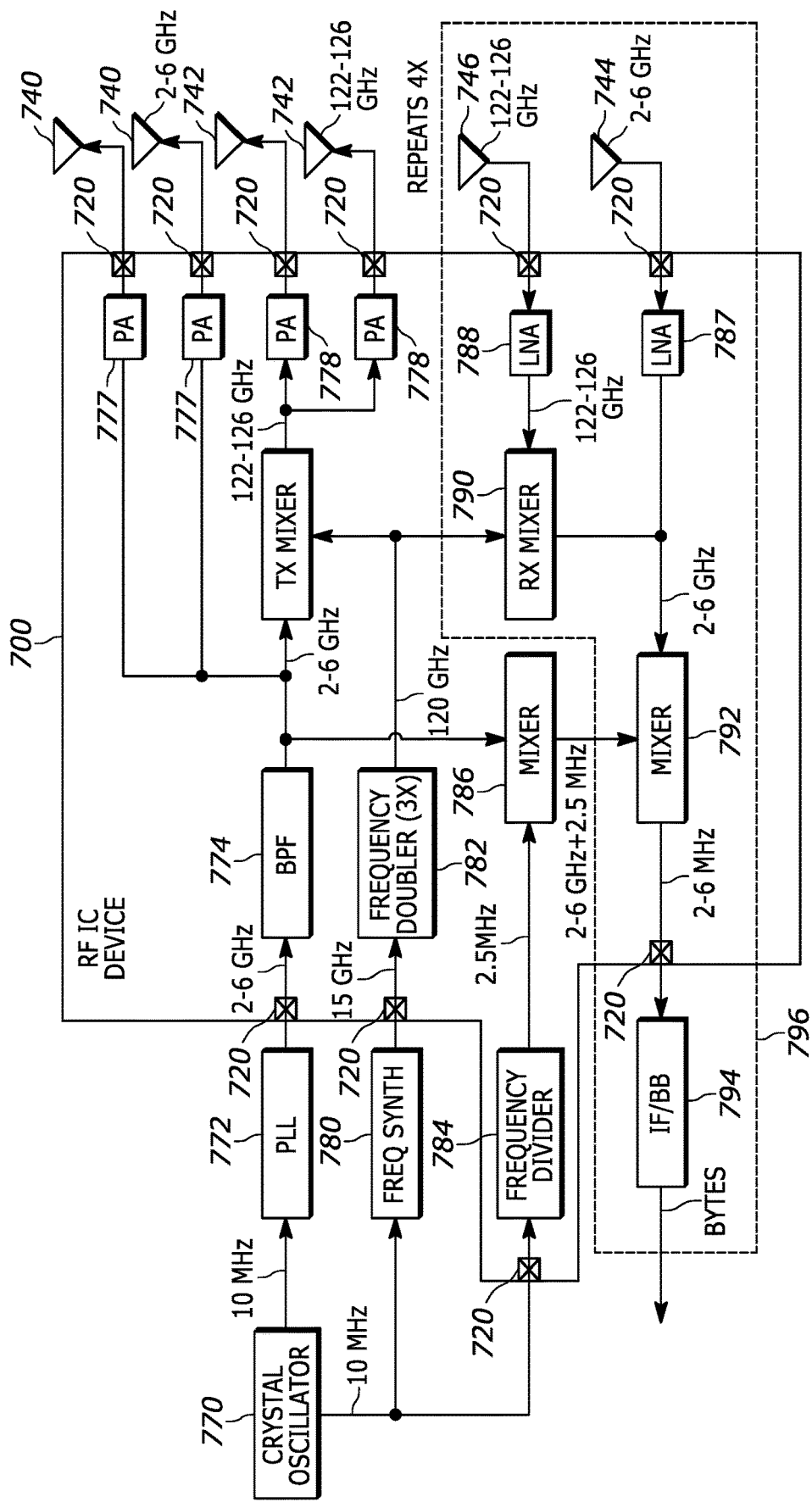
FIG. 7 depicts the system as shown in FIGS. 2A-2C and FIG. 6 with the boundary of the RF IC device identified with a solid line box.

FIG. 7 depicts the system as shown in FIGS. 2A-2C and FIG. 6 with a boundary identifying the RF IC device 700. FIG. 7 also identifies with a dashed line box 796, elements of the multi-band sensor system that repeat four times in an embodiment of the system that includes four receive paths for each of the low-band and the high-band operational modes.

Various techniques that can be implemented alone or in combination to isolate electrical signals that correspond to reflections from objects (e.g., such as blood) from other electrical signals that correspond to other reflections (e.g., such as reflections from bone and/or fibrous tissue such as muscle and tendons) and/or signals that correspond to leakage are described below. Such techniques relate to and/or involve, for example, transmission characteristics, beam-forming, Doppler effect processing, leakage mitigation, and antenna design.

Figure 8A:
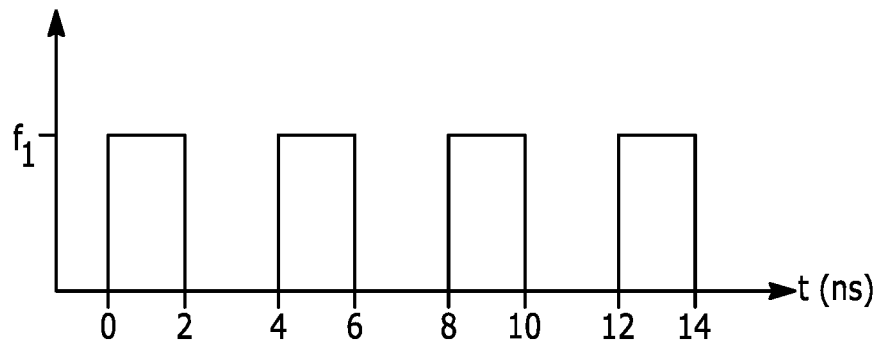
FIGS. 8A-8C depict frequency versus time graphs of impulse, chirp, and stepped frequency techniques for transmitting electromagnetic energy in a radar system.
Figure 8B:
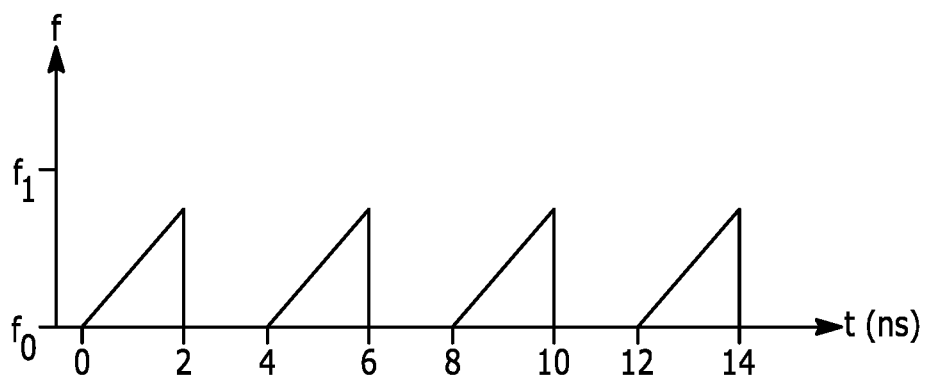
Figure 8C:
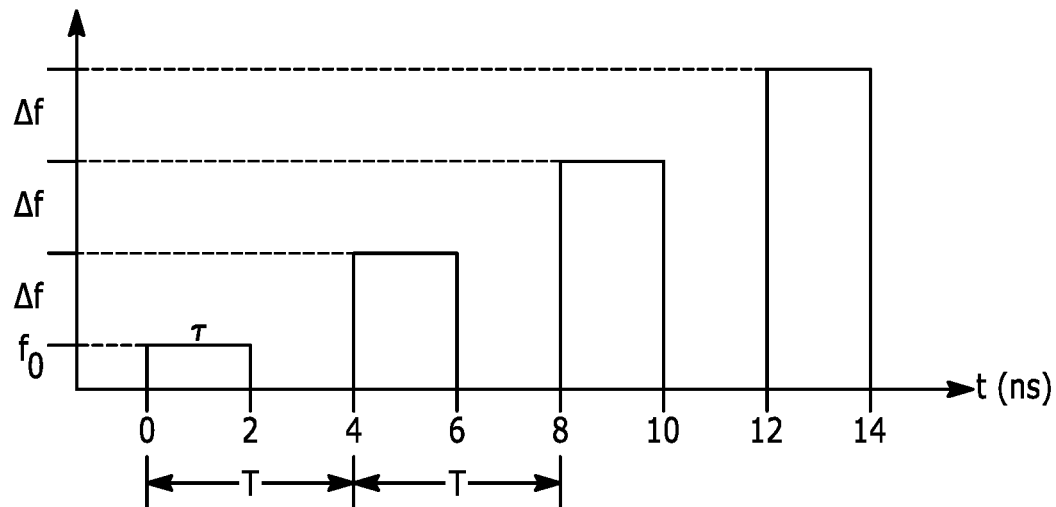

As is known in the field, radar detection involves transmitting electromagnetic energy and receiving reflected portions of the transmitted electromagnetic energy. Techniques for transmitting electromagnetic energy in radar systems include impulse, chirp, and stepped frequency techniques. FIGS. 8A-8C depict frequency versus time graphs of impulse, chirp, and stepped frequency techniques for transmitting electromagnetic energy in a radar system. FIG. 8A depicts a radar transmission technique that involves transmitting pulses of electromagnetic energy at the same frequency for each pulse, referred to as "impulse" transmission. In the example of FIG. 8A, each pulse is at frequency, $f_1$, and lasts for a constant interval of approximately 2 ns. The pulses are each separated by approximately 2 ns.

FIG. 8B depicts a radar transmission technique that involves transmitting pulses of electromagnetic energy at an increasing frequency for each interval, referred to herein as "chirp" transmission. In the example of FIG. 8B, each chirp increases in frequency from frequency $f_0$ to $f_1$ over an interval of 2 ns and each chirp is separated by 2 ns. In other embodiments, the chirps may be separated by very short intervals (e.g., a fraction of a nanosecond) or no interval.

FIG. 8C depicts a radar transmission technique that involves transmitting pulses of electromagnetic energy at the same frequency during a particular pulse but at an increased frequency from pulse-to-pulse, referred to herein as a "stepped frequency" transmission or a stepped frequency pattern. In the example of FIG. 8C, each pulse has a constant frequency over the interval of the pulse (e.g., over 2 ns), but the frequency increases by an increment of $\Delta f$ from pulse-to-pulse. For example, the frequency of the first pulse is $f_0$, the frequency of the second pulse is $f_0+\Delta f$, the frequency of the third pulse is $f_0+2\Delta f$, and the frequency of the fourth pulse is $f_0+3\Delta f$, and so on.

Figure 9:
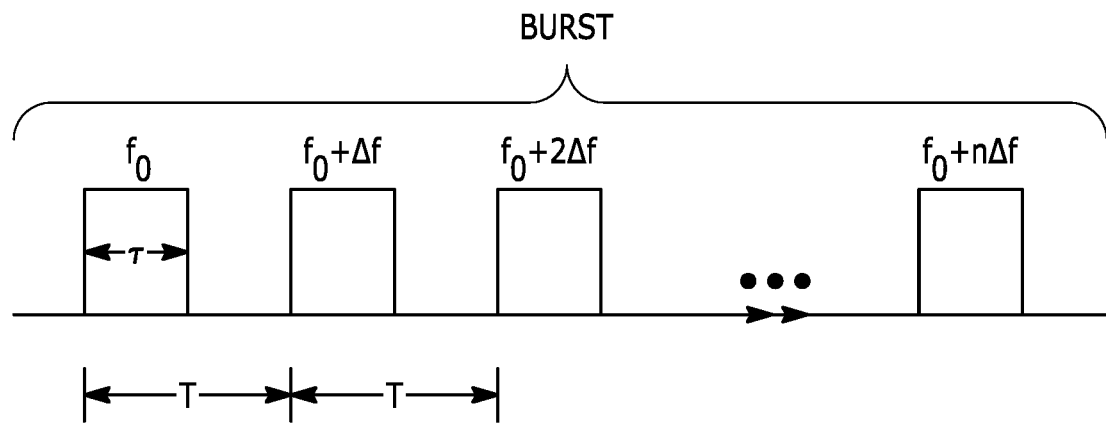
FIG. 9 depicts a burst of electromagnetic energy using stepped frequency transmission.

In an embodiment, the sensor systems described herein are operated using stepped frequency transmission. Operation of a sensor system using stepped frequency transmission is described in more detail below. FIG. 9 depicts a burst of electromagnetic energy using stepped frequency transmission. The frequency of the pulses in the burst can be expressed as:

$$f_n = f_0 + n\Delta f$$

where $f_0$=starting carrier frequency, $\Delta f$=step size, $\tau$=pulse length (active, per frequency), T=repetition interval, n=1, ... N, each burst consists of N pulses (frequencies) and a coherent processing interval (CPI)=N·T=1 full burst.

Using stepped frequency transmission enables relatively high range resolution. High range resolution can be advantageous when trying to monitor a health parameter such as the blood glucose level in a vein that may, for example, have a diameter in the range of 1-4 mm. For example, in order to effectively isolate a signal that corresponds to reflections of electromagnetic energy from the blood in a 1-4 mm diameter vein, it is desirable to have a high range resolution, which is provided by the 122-126 GHz frequency range.

Using stepped frequency transmission, range resolution can be expressed as:

$$\Delta R = c/2B$$

wherein c=speed of light, B=effective bandwidth. The range resolution can then be expressed as:

$$\Delta R = c/2N \cdot \Delta f$$

wherein $B = N \cdot \Delta f$. Thus, range resolution does not depend on instantaneous bandwidth and the range resolution can be increased arbitrarily by increasing $N \cdot \Delta f$.

Figure 10A:
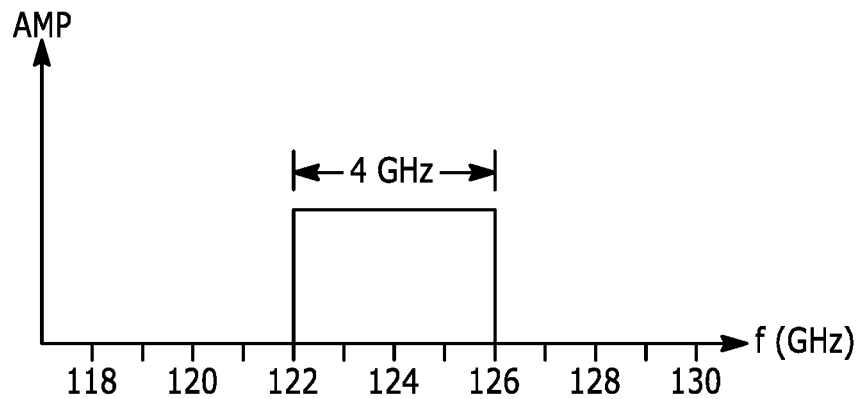
FIG. 10A depicts a graph of the transmission bandwidth, B, of transmitted electromagnetic energy in the frequency range of 122-126 GHz.
Figure 10B:
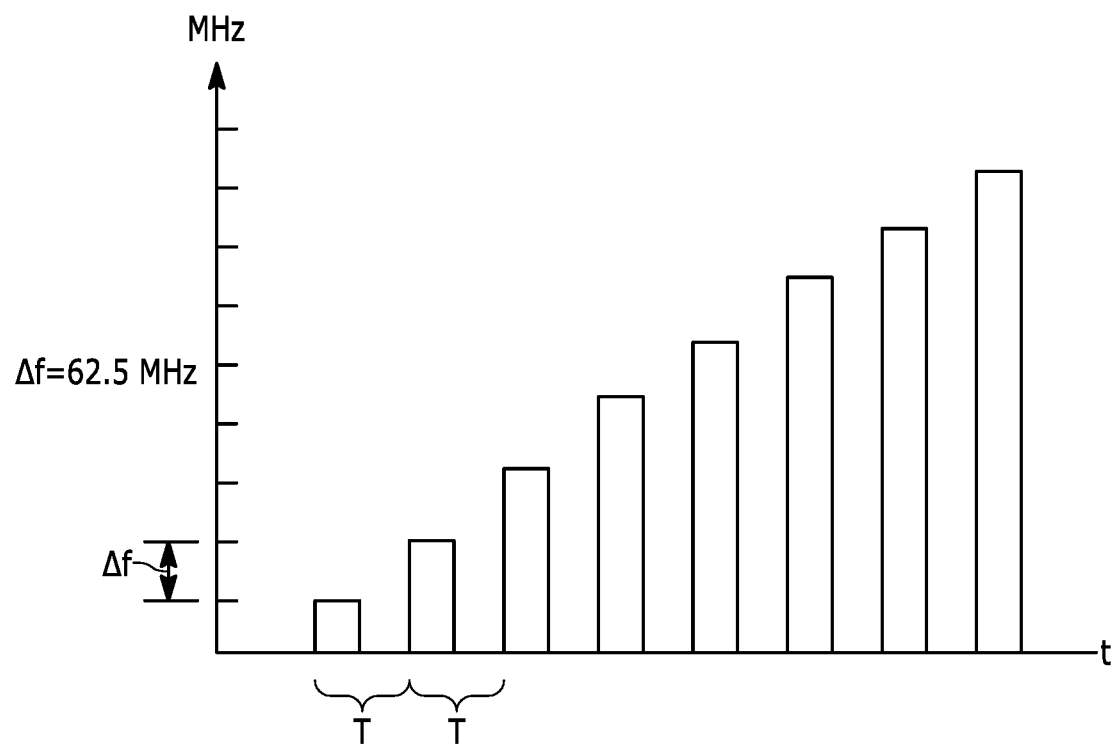
FIG. 10B depicts a graph of stepped frequency pulses that have a repetition interval, T, and a step size, $\Delta f$, of 62.5 MHz.

In an embodiment, the electromagnetic energy is transmitted from the high-band TX antennas in the frequency range of approximately 122-126 GHz, which corresponds to a total bandwidth of approximately 4 GHz, e.g., B=4 GHz. FIG. 10A depicts a graph of the transmission bandwidth, B, of transmitted electromagnetic energy in the frequency range of 122-126 GHz. Within a 4 GHz bandwidth, from 122-126 GHz, discrete frequency pulses can be transmitted. For example, in an embodiment, the number of discrete frequencies that can be transmitted ranges from, for example, 64-256 discrete frequencies. In a case with 64 discrete frequency pulses and a repetition interval, T, over 4 GHz of bandwidth, the step size, $\Delta f$, is 62.5 MHz (e.g., 4 GHz of bandwidth divided by 64=62.5 MHz) and in a case with 256 discrete frequency pulses and a repetition interval, T, over 4 GHz of bandwidth, the step size, $\Delta f$, is 15.625 MHz (e.g., 4 GHz of bandwidth divided by 256=15.625 MHz). FIG. 10B depicts a graph of stepped frequency pulses that have a repetition interval, T, and a step size, $\Delta f$, of 62.5 MHz (e.g., 4 GHz of bandwidth divided by 64=62.5 MHz). As described above, an example sensor system has four band-specific RX antennas. Assuming a discrete frequency can be received on each RX antenna, degrees of freedom (DOF) of the sensor system in the receive operations can be expressed as: 4 RX antennas×64 discrete frequencies=256 DOF; and 4 RX antennas×256 discrete frequencies=1K DOF. The number of degrees of freedom (also referred to as "transmission frequency diversity") can provide signal diversity, which can be beneficial in an environment such as the anatomy of a person. For example, the different discrete frequencies may have different responses to the different anatomical features of the person. Thus, greater transmission frequency diversity can translate to greater signal diversity, and ultimately to more accurate health monitoring.

Figure 11A:
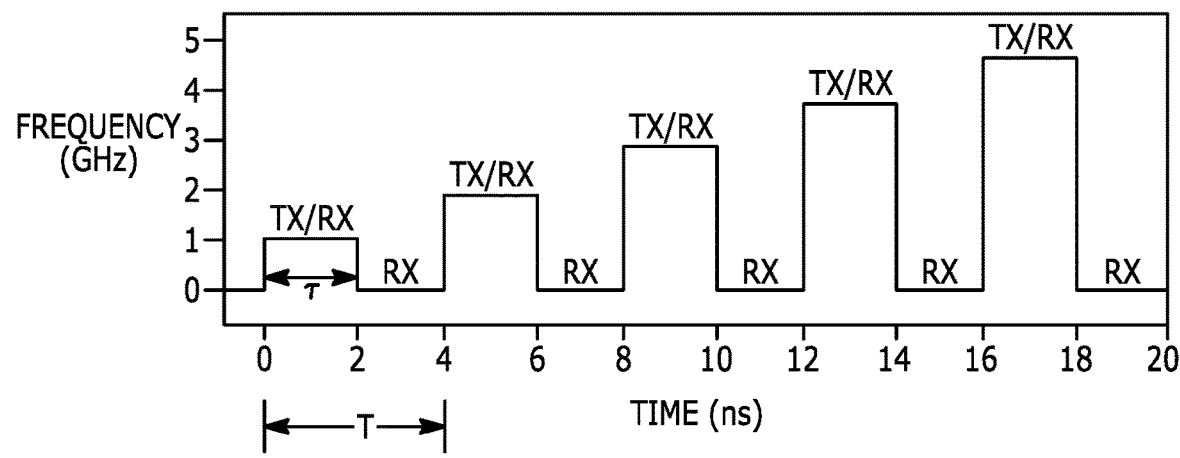
FIG. 11A depicts a frequency versus time graph of transmission pulses, with transmit (TX) interval and receive (RX) intervals identified relative to the pulses.
Figure 11B:
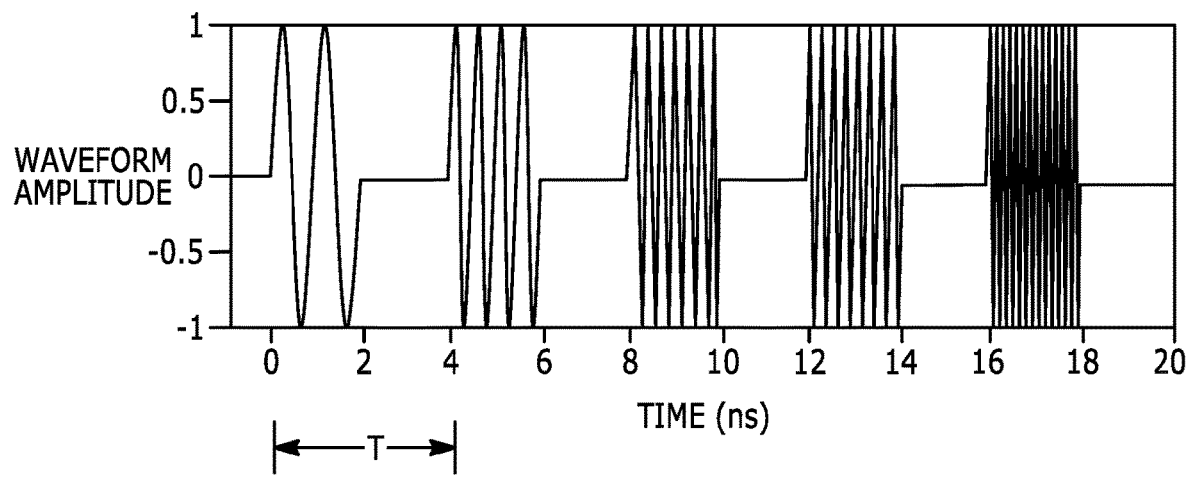
FIG. 11B depicts an amplitude versus time graph of the transmission waveforms that corresponds to FIG. 16A.

One feature of a stepped frequency transmission approach is that the sensor system receives reflected electromagnetic energy at basically the same frequency over the repetition interval, T. That is, as opposed to chirp transmission, the frequency of the pulse does not change over the interval of the pulse and therefore the received reflected electromagnetic energy is at the same frequency as the transmitted electromagnetic energy for the respective interval. FIG. 11A depicts a frequency versus time graph of transmission pulses, with transmit (TX) and receive (RX) intervals identified relative to the pulses. As illustrated in FIG. 11A, RX operations for the first pulse occur during the pulse length, $\tau$, of repetition interval, T, and during the interval between the next pulse. FIG. 11B depicts an amplitude versus time graph of the transmission waveforms that corresponds to FIG. 11A. As illustrated in FIG. 11B, the amplitude of the pulses is constant while the frequency increases by $\Delta f$ at each repetition interval, T.

In an embodiment, the power of the transmitted electromagnetic energy can be set to achieve a desired penetration depth and/or a desired illumination volume. In an embodiment, the transmission power from the high-band TX antennas is about 15 dBm and the transmission power for the low-band TX antennas is about 20 dBm.

In an embodiment, electromagnetic energy can be transmitted from the TX antennas one TX antenna at a time (referred to herein as "transmit diversity"). For example, a signal is transmitted from a first one of the two TX antennas while the second one of the two TX antennas is idle and then a signal is transmitted from the second TX antenna while the first TX antenna is idle. Transmit diversity may reveal that illumination from one of the two TX antennas provides a higher quality signal than illumination from the other of the two TX antennas. This may be especially true when trying to illuminate a vein whose location may vary from person to person and/or from moment to moment (e.g., depending on the position of the wearable device relative to the vein). Thus, transmit diversity can provide sets of received signals that are independent of each other and may have different characteristics, e.g., signal power, SNR, etc.

Some theory related to operating the sensor system using a stepped frequency approach is described with reference to FIG. 12, which illustrates operations related to transmitting, receiving, and processing phases of the sensor system operation. With reference to the upper portion of FIG. 12, a time versus amplitude graph of a transmitted signal burst, similar to the graph of FIG. 16B, is shown. The graph represents the waveforms of five pulses of a burst at frequencies of $f_0$, $f_0 + \Delta f$, $f_0 + 2\Delta f$, $f_0 + 3\Delta f$, and $f_0 + 4\Delta f$.

Figure 12:
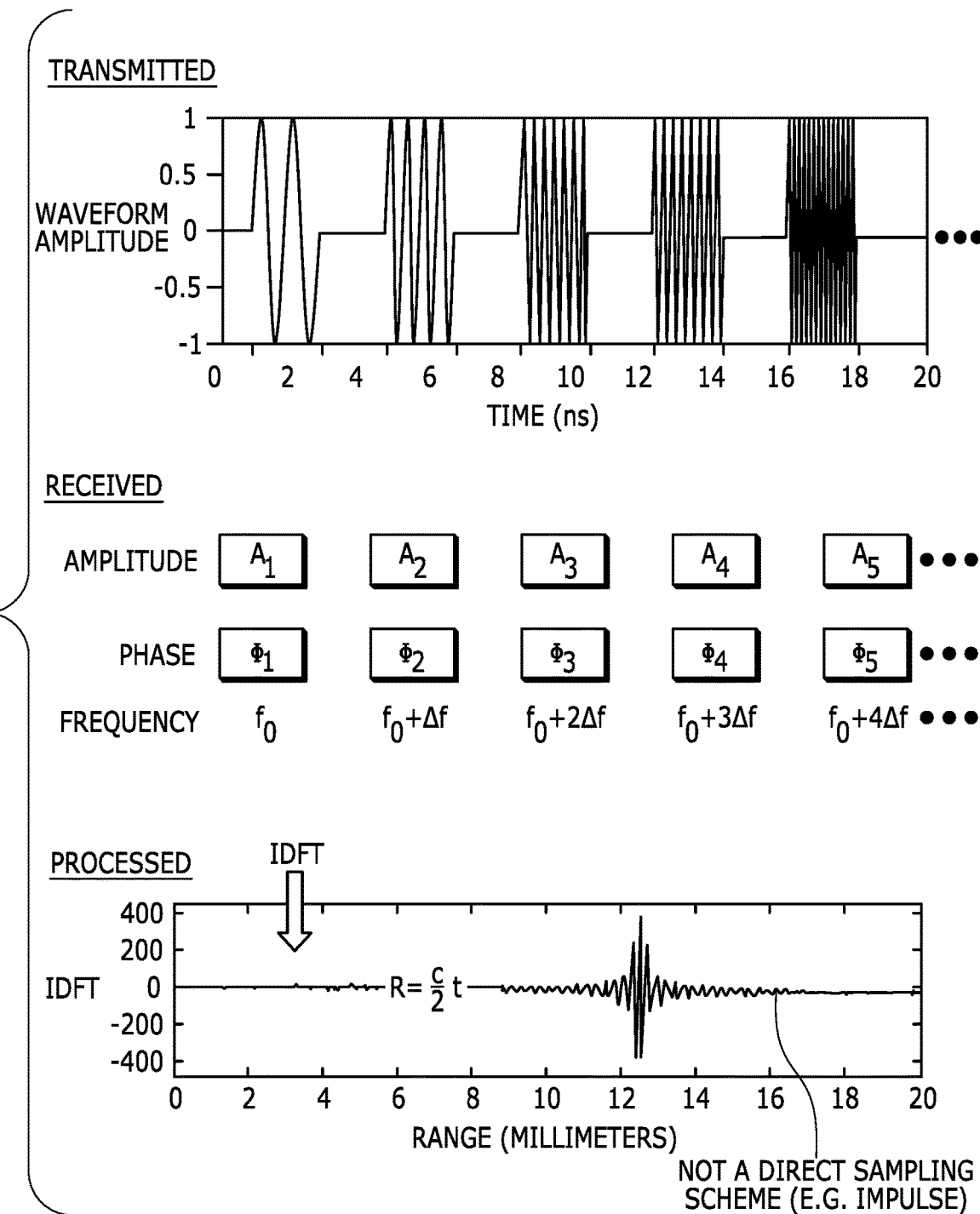
FIG. 12 illustrates operations related to transmitting, receiving, and processing phases of the sensor system operation.

The middle portion of FIG. 12 represents values of received signals that correspond to the amplitude, phase, and frequency of each pulse in the burst of four pulses. In an embodiment, received signals are placed in range bins such that there is one complex sample per range bin per frequency. Inverse Discrete Fourier Transforms (IDFTs) are then performed on a per-range bin basis to determine range information. The bottom portion of FIG. 12 illustrates an IDFT process that produces a signal that corresponds to the range of a particular object. For example, the range may correspond to a vein such as the basilic vein. In an embodiment, some portion of the signal processing is performed digitally by a DSP or CPU. Although one example of a signal processing scheme is described with reference to FIG. 12, other signal processing schemes may be implemented to isolate signals that correspond to reflections from blood in a vein (such as the basilic vein) from signals that correspond to reflections from other undesired anatomical features (such as tissue and bones) and from signals that correspond to leakage from the TX antennas.

Beamforming is a signal processing technique used in sensor arrays for directional signal transmission and/or reception. Beamforming can be implemented by combining elements in a phased antenna array in such a way that signals at particular angles experience constructive interference while other signals experience destructive interference. Beamforming can be used in both transmit operations and receive operations in order to achieve spatial selectivity, e.g., to isolate some received signals from other received signals. In an embodiment, beamforming techniques are utilized to isolate signals that correspond to reflections from blood in a vein (such as the basilic vein) from signals that correspond to reflections from other undesired anatomical features (such as tissue and bones) and from signals that correspond to leakage from the TX antennas.

Figure 13:
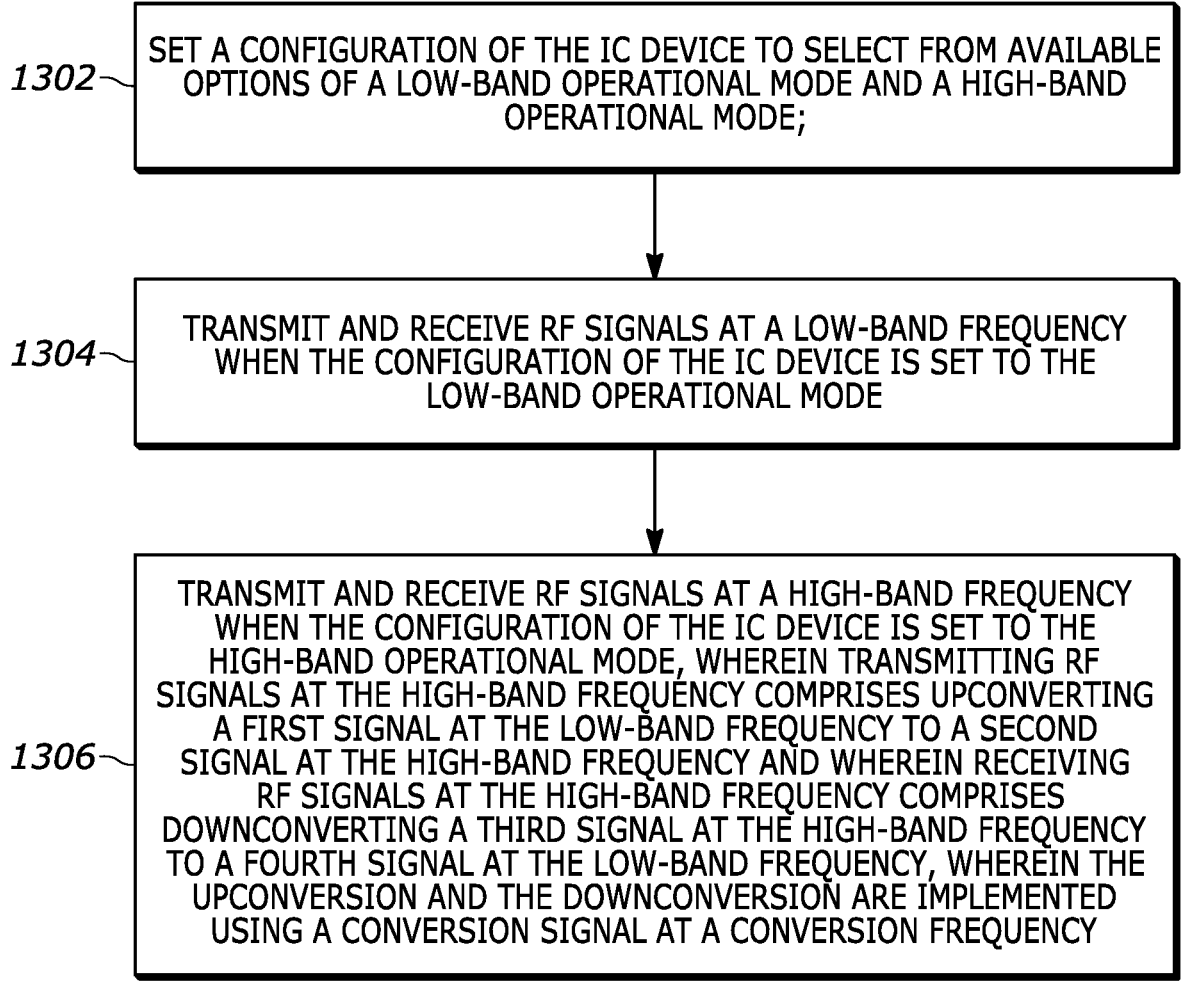
FIG. 13 is a process flow diagram of a method for operating an integrated circuit device.

FIG. 13 is a process flow diagram of a method for operating an IC device. At block 1302, a configuration of the IC device is set to select from available options of a low-band operational mode and a high-band operational mode. At block 1304, RF signals are transmitted and received at a low-band frequency when the configuration of the IC device is set to the low-band operational mode, and at block 1306, RF signals are transmit and received at a high-band frequency when the configuration of the IC device is set to the high-band operational mode, wherein transmitting RF signals at the high-band frequency comprises upconverting a first signal at the low-band frequency to a second signal at the high-band frequency and wherein receiving RF signals at the high-band frequency comprises downconverting a third signal at the high-band frequency to a fourth signal at the low-band frequency, wherein the upconversion and the downconversion are implemented using a conversion signal at a conversion frequency.

In an embodiment, it is desirable for high-band antennas (e.g., antennas tuned for the 122-126 GHz band) to be very close to the corresponding PAs (e.g., 278, FIG. 2) and LNAs (e.g., 288, FIG. 2) in order to reduce noise. Thus, in some embodiments, the high-band TX antennas and RX antennas are attached to the packaged IC device. In an embodiment, high-band TX and RX antennas (e.g., TX antennas 642 and RX antennas 646, FIG. 6) are attached to an outer surface of the semiconductor substrate and/or to an outer surface of an IC package and electrically connected to the circuits integrated into the semiconductor substrate. In an embodiment, the high-band TX and RX antennas are attached to the outer surface of the IC package such that the TX and RX antenna attachments points are very close (e.g., 0.5-5 mm) to the corresponding transmit and receive circuits such as the PAs and LNAs. In an embodiment, the semiconductor substrate and the packaged IC device includes outputs for outputting electrical signals to other components such as a DSP, a CPU, and or a bus. In some embodiments, the packaged IC device may include the DSP and/or CPU or the packaged IC device may include some DSP and/or CPU functionality.

In an embodiment, a packaged IC device has dimensions of 5 mm×5 mm (e.g., referred to as the device "footprint") and the semiconductor substrate has a footprint that is slightly smaller than the footprint of the packaged IC device, e.g., the semiconductor substrate has dimensions of approximately 0.1-1 mm less than the packaged IC device on each side. In an example embodiment, the packaged IC device has a thickness of approximately 0.3-2 mm and the semiconductor substrate has a thickness in the range of about 0.1-0.7 mm. In an embodiment, the high-band TX and RX antennas are designed for millimeter range radio waves, for example, radio waves of 122-126 GHz have wavelengths in the range of 2.46 to 2.38 mm. TX and RX antennas for the low-band operational mode may be farther away from the IC device and connected by conductive traces because the longer wavelength is not as sensitive to noise and/losses as the 122-126 GHz band. In an embodiment, the high-band TX and RX antennas (e.g., 122-126 GHz) are microstrip patch antennas and the dimensions of the antennas are a function of the wavelength of the radio waves. In some embodiments, microstrip patch antennas have length and width dimensions of one-half the wavelength of the target radio waves. Thus, microstrip patch antennas designed for radio waves of 122-126 GHz (e.g., wavelengths in the range of 2.46 to 2.38 mm) may have length and width dimensions of around 1.23-1.19 mm, but no more than 1.3 mm. Other types of antennas such as dipole antennas are also possible. In an embodiment, the small antenna size of the high-band antennas makes it advantageous to attach all six of the high-band antennas (e.g., two TX antennas and four RX antennas) to the top surface of the package of the IC device within the footprint of the semiconductor substrate, which makes the packaged IC device very compact.

In an embodiment, the high-band RX antennas form a phased antenna array and for an application such as health monitoring it may be desirable to have as much spatial separation as possible between the RX antennas to improve overall signal quality by obtaining unique signals from each RX antenna (this may be true for both the high-band antennas and the low-band antennas). For example, spatial separation of the high-band RX antennas enables improved depth discrimination to isolate signals that correspond to reflections from an object (e.g., blood in a vein) from reflections from other objects. Thus, in an embodiment, the high-band RX antennas are located at the corners of a rectangular shaped IC device. For example, the high-band RX antennas are located flush with the corners of a semiconductor substrate and/or flush with the corners of an IC device package or within less than about 0.5 mm from the corners of the semiconductor substrate and/or from the corners of the IC device package.

In an embodiment, the high-band TX antennas are located on opposite sides of the RF IC device approximately in the middle between the two high-band RX antennas that are on the same side. At extremely high frequencies (e.g., 30-300 GHz) conductor losses can be very significant. Additionally, conductor losses at extremely high frequencies are known to be frequency-dependent, with higher frequencies exhibiting higher conductor losses. In many health monitoring applications, power, such as battery power, is a limited resource that must be conserved. Additionally, for reasons as described above such as limiting undesired reflections, low power transmissions may be desirable for health monitoring reasons. Because of the low power environment, conductor losses can severely impact performance of the sensor system. For example, significant conductor losses can occur between the antennas and the conductive pads of the semiconductor substrate, or "die," and between the conductive pads and the transmit/receive components in the die, e.g., the channel-specific circuits such as amplifiers, filters, mixers, etc. In order to reduce the impact of conductor losses in the sensor system, it is important to locate the antennas as close to the channel-specific transmit/receive components of the die as possible. In an embodiment, the high-band transmit and receive components (e.g., the high-band PAs and LNAs) are strategically fabricated on the semiconductor substrate in locations that correspond to the desired locations of the antennas. Thus, when the high-band TX and RX antennas are physically and electrically attached to the IC device, the high-band TX and RX antennas are as close as possible to the transmit and receive components on the die, e.g., collocated such that a portion of the channel specific transmit/receive component overlaps from a plan view perspective a portion of the respective TX/RX antenna. Such a collocated configuration enables the desired distribution of the high-band TX and RX antennas to be maintained while effectively managing conductor losses in the system. Such a close proximity between antennas and channel-specific circuits of the die is extremely important at frequencies in the 122-126 GHz range and provides an improvement over sensor systems that include conductive traces of multiple millimeters between the antennas and the die.

As used herein "low-band," "medium-band," and "high-band" are relative terms. In particular, the bands are "low," "medium," or "high" in frequency relative to the other bands that the IC device is configured to implement. For example, a "low-band" of 2-6 GHz is lower in frequency than a "high-band" of 122-126 GHz and a "medium-band" of 22-26 GHz is higher in frequency than a "low-band" (e.g., 2-6 GHz) and lower in frequency than a "high-band" (e.g., 122-126 GHz).

In an embodiment, a multi-band sensor system may be desirable for health monitoring applications. For example, multiple different bands may improve the quality of monitoring a particular parameter and/or multiple different bands may enable higher quality monitoring of multiple different health parameters. For example, one band may provide better results for monitoring a particular health parameter (such as blood glucose level), while a different band may provide better results for monitoring a different health parameter (such as blood pressure or heart rate). Thus, a multi-band stepped frequency radar based sensor system enables health monitoring at multiple different frequency bands with the same RF IC device. Additionally, a multi-band sensor system may be desirable for other stepped frequency radar based sensing applications, such as security monitoring, including weapon detection.

Although certain frequency bands/ranges are described, in some embodiments, the bands/ranges are substantially at the enumerated bands/frequencies, e.g., within ±10%, ±5%, or ±1%, of the enumerated bands/frequencies. Although certain frequency combinations for frequency generation are described, other frequency combinations are possible. For example, the base frequency may be a frequency other than 10 MHz. Additionally, the conversion signal may be generated from the base signal using a different frequency combination.

In an embodiment, a multi-band sensor system includes components to control the operational mode of the system according to a selected mode. Components may include selection logic, signal paths, and power control components. Power control components may include circuits to reduce the power to certain components, increase the power to components, power gate components or other techniques that are known in the field to manage power consumption.

In an embodiment, PAs and LNAs are tuned to provide desirable performance at particular frequency bands. For example, PAs and/or LNAs may include components/elements with physical parameters (e.g., dimensions, conductivity, dielectric qualities, etc.) that are band-specific.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Alternatively, embodiments of the invention may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An integrated circuit device comprising:
   transmit components and receive components;
   at least one low-band transmit interface connected to a first transmit component to output a first signal at a low-band frequency;
   at least one high-band transmit interface connected to a second transmit component to output a second signal at a high-band frequency;
   at least one low-band receive interface connected to a first receive component to receive a third signal at the low-band frequency;
   at least one high-band receive interface connected to a second receive component to receive a fourth signal at the high-band frequency; and
   mixers connected to upconvert the first signal at the low-band frequency to the second signal at the high-band frequency for transmission from the high-band transmit interface and to downconvert the fourth signal at the high-band frequency received at the high-band receive interface to a fifth signal at the low-band frequency, wherein the upconversion and the downconversion are implemented using a conversion signal at a conversion frequency.

2. The integrated circuit device of claim 1, wherein the low-band frequency is in the range of 2-6 GHz, the high-band frequency is in the range of 122-126 GHz, and the conversion frequency is 120 GHz.

3. The integrated circuit device of claim 1, wherein the low-band frequency is in the range of 2-6 GHz, the high-band frequency is in the range of 22-26 GHz, and the conversion frequency is 20 GHz.

4. The integrated circuit device of claim 1, further comprising a second receive mixer connected to upconvert the first signal at the low-band frequency with an intermediate frequency to output a sixth signal at the low-band frequency plus the intermediate frequency.

5. The integrated circuit device of claim 4, further comprising a third receive mixer connected to downconvert the third signal at the low-band frequency and the fifth signal at the low-band frequency with the sixth signal at the low-band frequency plus the intermediate frequency to produce a seventh signal at the intermediate frequency.

6. The integrated circuit device of claim 1, further comprising:
   a second receive mixer connected to upconvert the first signal at the low-band frequency with an intermediate frequency to output a sixth signal at the low-band frequency plus the intermediate frequency;
   a third receive mixer connected to downconvert the third signal at the low-band frequency and the fifth signal at the low-band frequency with the sixth signal at the low-band frequency plus the intermediate frequency to produce a seventh signal at the intermediate frequency; and
   a baseband interface connected to receive the seventh signal.

7. The integrated circuit device of claim 6, wherein the low-band frequency is in the range of 2-6 GHz, the high-band frequency is in the range of 122-126 GHz, and the conversion frequency is 120 GHz.

8. The integrated circuit device of claim 7, wherein the first signal is stepped across the 2-6 GHz frequency range.

9. The integrated circuit device of claim 8, wherein the intermediate frequency is 2.5 MHz.

10. The integrated circuit device of claim 6, wherein the low-band frequency is in the range of 2-6 GHz, the high-band frequency is in the range of 22-26 GHz, and the conversion frequency is 20 GHz.

11. The integrated circuit device of claim 10, wherein the first signal is stepped across the 2-6 GHz frequency range.

12. The integrated circuit device of claim 11, wherein the intermediate frequency is 2.5 MHz.

13. The integrated circuit device of claim 1, wherein the transmit components, the receive components, and the mixers are fabricated into a semiconductor substrate of the integrated circuit device.

14. The integrated circuit device of claim 13, wherein the transmit components include power amplifiers and the receive components include low-noise amplifiers.

15. The integrated circuit device of claim 1, further comprising a frequency multiplier configured to generate the conversion signal at the conversion frequency from a pre-conversion signal at a pre-conversion frequency.

16. An integrated circuit device comprising:
transmit components and receive components;
at least one low-band transmit interface connected to a first transmit component to output a first signal at a low-band frequency;
at least one high-band transmit interface connected to a second transmit component to output a second signal at a high-band frequency;
at least one low-band receive interface connected to a first receive component to receive a third signal at the low-band frequency;
at least one high-band receive interface connected to a second receive component to receive a fourth signal at the high-band frequency; and
means for upconverting the first signal at the low-band frequency to the second signal at the high-band frequency for transmission from the high-band transmit interface and downconverting the fourth signal at the high-band frequency received at the high-band receive interface to a fifth signal at the low-band frequency, wherein the upconversion and the downconversion are implemented using a conversion signal at a conversion frequency.

17. An integrated circuit device comprising:
transmit components and receive components;
at least one low-band transmit interface connected to a first transmit component to output a first signal at a low-band frequency;
at least one high-band transmit interface connected to a second transmit component to output a second signal at a high-band frequency;
at least one low-band receive interface connected to a first receive component to receive a third signal at the low-band frequency;
at least one high-band receive interface connected to a second receive component to receive a fourth signal at the high-band frequency;
a transmit mixer connected to upconvert the first signal at the low-band frequency to the second signal at the high-band frequency for transmission from the high-band transmit interface; and
a receive mixer connected to downconvert the fourth signal at the high-band frequency received at the high-band receive interface to a fifth signal at the low-band frequency;
wherein the transmit mixer and the receive mixer are connected to receive a conversion signal at a conversion frequency.

18. An integrated circuit device comprising:
transmit components and receive components;
at least one low-band transmit interface connected to a first transmit component to output a first signal at a low-band frequency;
at least one medium-band transmit interface connected to a second transmit component to output a second signal at a medium-band frequency;
at least one high-band transmit interface connected to a third transmit component to output a third signal at a high-band frequency;
at least one low-band receive interface connected to a first receive component to receive a fourth signal at the low-band frequency;
at least one medium-band receive interface connected to a second receive component to receive a fifth signal at the medium-band frequency;
at least one high-band receive interface connected to a third receive component to receive a sixth signal at the high-band frequency; and
mixers connected to upconvert the first signal at the low-band frequency to the second signal at the medium-band frequency for transmission from the medium-band transmit interface, or to upconvert the first signal at the low-band frequency to the third signal at the high-band frequency for transmission from the high-band transmit interface, and to downconvert the fifth signal at the medium-band frequency received at the medium-band receive interface to a seventh signal at the low-band frequency or to downconvert the sixth signal at the high-band frequency received at the high-band receive interface to an eighth signal at the low-band frequency, wherein the upconversion and the downconversion corresponding to the medium-band frequency are implemented using a conversion signal at a first conversion frequency and wherein the upconversion and the downconversion corresponding to the high-band frequency are implemented using a conversion signal at a second conversion frequency.

19. The integrated circuit device of claim 18, wherein the low-band frequency is in the range of 2-6 GHz, the medium-frequency is in the range of 22-26 GHz, the high-band frequency is in the range of 122-126 GHz, the first conversion frequency is 20 GHz, and the second conversion frequency is 120 GHz.

20. The integrated circuit device of claim 18, further comprising a second receive mixer connected to upconvert the first signal at the low-band frequency with an intermediate frequency to output a ninth signal at the low-band frequency plus the intermediate frequency.

21. The integrated circuit device of claim 19, further comprising a third receive mixer connected to downconvert the fourth signal at the low-band frequency, the seventh signal at the low-band frequency, or the eighth signal at the low-band frequency with the ninth signal at the low-band frequency plus the intermediate frequency to produce a tenth signal at the intermediate frequency.

22. The integrated circuit device of claim 21, further comprising a baseband interface connected to receive the tenth signal at the intermediate frequency.

23. A radio frequency system comprising:
a radio frequency (RF) integrated circuit (IC) device including:
  transmit components and receive components;
  at least one low-band transmit interface connected to a first transmit component to output a first signal at a low-band frequency;
  at least one high-band transmit interface connected to a second transmit component to output a second signal at a high-band frequency;
  at least one low-band receive interface connected to a first receive component to receive a third signal at the low-band frequency;
  at least one high-band receive interface connected to a second receive component to receive a fourth signal at the high-band frequency;
  mixers connected to upconvert the first signal at the low-band frequency to the second signal at the high-band frequency for transmission from the high-band transmit interface and to downconvert the fourth signal at the high-band frequency received at the high-band receive interface to a fifth signal at the low-band frequency, wherein the upconversion and the downconversion are implemented using a conversion signal at a conversion frequency;
a low-band transmit antenna connected to the at least one low-band transmit interface and tuned to the low-band frequency;
a high-band transmit antenna connected to the at least one high-band transmit interface and tuned to the high-band frequency;
a low-band receive antenna connected to the at least one low-band receive interface and tuned to the low-band frequency;
a high-band receive antenna connected to the at least one high-band receive interface and tuned to the high-band frequency.

24. The radio frequency system of claim 23, further comprising a second receive mixer connected to upconvert the first signal at the low-band frequency with an intermediate frequency to output a sixth signal at the low-band frequency plus the intermediate frequency.

25. The radio frequency system of claim 24, further comprising a third receive mixer connected to downconvert the third signal at the low-band frequency and the fifth signal at the low-band frequency with the sixth signal at the low-band frequency plus the intermediate frequency to produce seventh signal at the intermediate frequency.

26. The radio frequency system of claim 25, wherein the RF IC device further includes a baseband interface connected to receive the seventh signal and further comprising a baseband component connected to the baseband interface of the RF IC device.

27. The radio frequency system of claim 26, further comprising a first signal source configured to generate the first signal at the low-band frequency.

28. The radio frequency system of claim 27, further comprising a second signal source configured to generate a pre-conversion signal at a pre-conversion frequency, the RF IC further comprising a frequency multiplier that is configured to generate the conversion signal at the conversion frequency from the pre-conversion signal at the pre-conversion frequency.

29. The radio frequency system of claim 28, further comprising an electronic oscillator configured to generate a source signal at a base frequency.

30. The radio frequency system of claim 29, wherein the first signal at the low-band frequency, the pre-conversion signal at the pre-conversion frequency, and the intermediate frequency are generated from the source signal at the base frequency.

31. The radio frequency system of claim 23, wherein the transmit components, the receive components, and the mixers are fabricated into the semiconductor substrate.

32. The radio frequency system of claim 31, wherein the transmit components include power amplifiers and the receive components include low-noise amplifier.

* * * * *